(12) United States Patent
Trucco et al.

(10) Patent No.: US 7,981,040 B2
(45) Date of Patent: Jul. 19, 2011

(54) METHOD OF ULTRASONIC DETECTION AND LOCALIZATION OF CONTRAST AGENT MICROBUBBLES AND METHOD FOR LOCAL DRUG ADMINISTRATION BY USING MICROBUBBLE CARRIERS

(75) Inventors: Andrea Trucco, Genoa (IT); Daniele Cecchini, Genoa (IT); Luca Di Resta, Salerno (IT)

(73) Assignee: ESAOTE, S.p.A., Milan (IT)

( * ) Notice: Subject to any disclaimer, the term of this patent is extended or adjusted under 35 U.S.C. 154(b) by 1496 days.

(21) Appl. No.: 11/404,271

(22) Filed: Apr. 14, 2006

(65) Prior Publication Data

US 2007/0016051 A1    Jan. 18, 2007

(30) Foreign Application Priority Data

Apr. 14, 2005 (EP) .................................... 05425222

(51) Int. Cl.
*A61B 8/14* (2006.01)

(52) U.S. Cl. ........ 600/458; 600/437; 600/408; 600/407; 600/443; 600/439

(58) Field of Classification Search .................. 600/407, 600/408, 437, 439, 443, 458
See application file for complete search history.

(56) References Cited

U.S. PATENT DOCUMENTS

| 5,140,670 | A | 8/1992 | Chua et al. |
| 5,526,816 | A | 6/1996 | Arditi |
| 5,776,063 | A | 7/1998 | Dittrich et al. |
| 2002/0055680 | A1 * | 5/2002 | Miele et al. ................... 600/450 |
| 2003/0167003 | A1 | 9/2003 | Masotti et al. |
| 2004/0006266 | A1 * | 1/2004 | Ustuner et al. ................ 600/407 |

FOREIGN PATENT DOCUMENTS

| EP | 1 341 003 A2 | 9/2003 |
| EP | 1 345 145 A2 | 9/2003 |
| EP | 05425222.6 | 10/2006 |
| WO | WO 2005/020132 A1 | 3/2005 |

OTHER PUBLICATIONS

N. de Jong et al., "Contrast Harmonic Imaging", Ultrasonics 40, pp. 567-573 (2002).
M. Ahmed et al., "Tissue Characterization Using Radial Transform and Higher Order Statistics", Nordic Signal Processing Symposium, (Jun. 2000).
J.M.. Mendel, "Tutorial on Higher-Order Statistics (Spectra) in Signal Processing and System Theory: Theoretical Results and Some Ap[placations", Proceedings of the IEEE, vol. 79 No. 3, pp. 278-304 (Mar. 1991).

* cited by examiner

*Primary Examiner* — Brian Casler
*Assistant Examiner* — Joel M Lamprecht
(74) *Attorney, Agent, or Firm* — Woodard, Emhardt, Moriarty, McNett & Henry LLP

(57) ABSTRACT

A method of ultrasonic detection and localization of contrast agent microbubbles wherein the decision as to whether or not the received ultrasonic signals indicate the presence of a single microbubble or a small microbubble population is made by analyzing the projections of the spectra of said received ultrasonic signals in multidimensional spaces, and by comparing such projections with the projections in said multidimensional spaces of sample control signals corresponding to known conditions of presence and/or absence of single microbubbles and/or small microbubble populations.

14 Claims, 18 Drawing Sheets

Bispectrum for simple tissue

Bispectrum for tissue + bubble

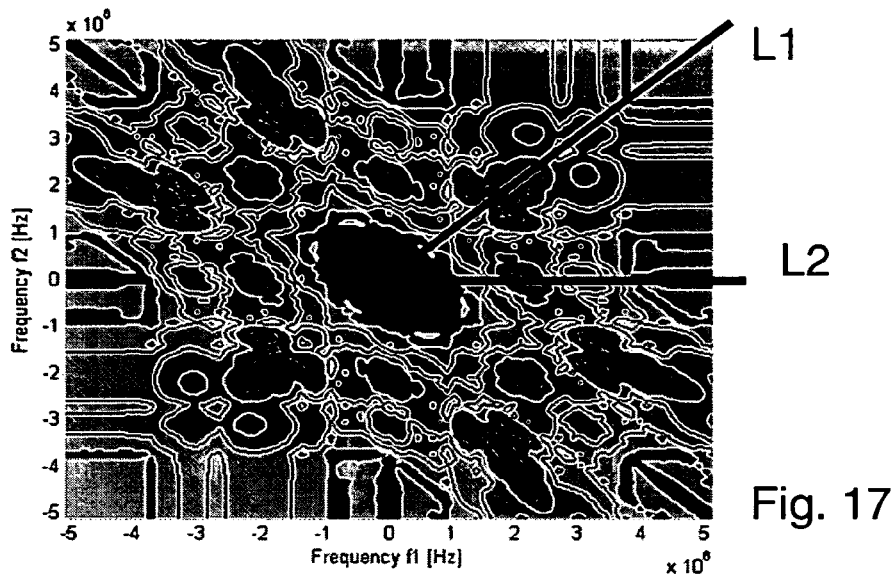
Fig. 17
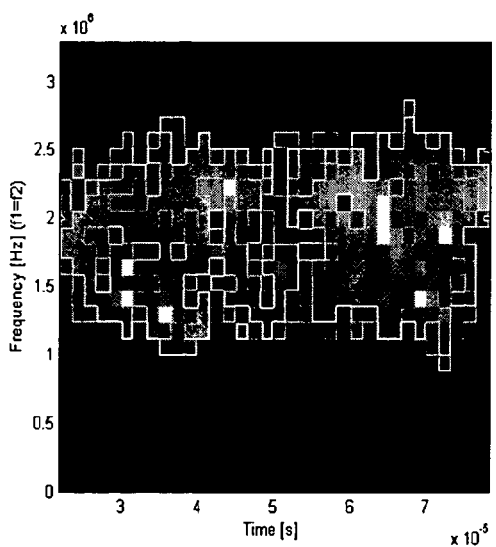
Fig. 18 Simple tissue
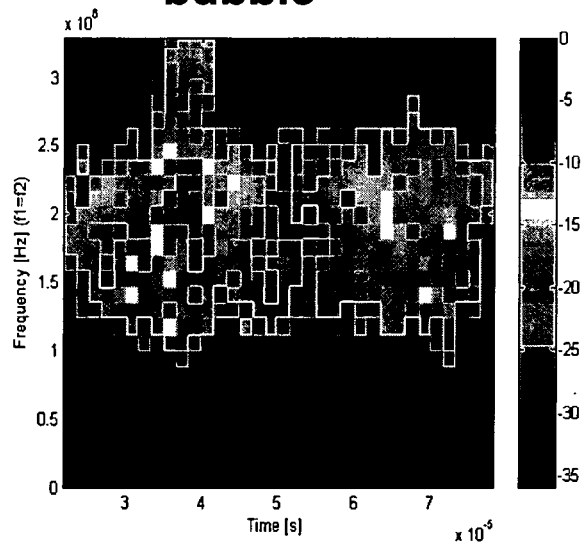
Fig. 19 Tissue + bubble
Bispectrum along the diagonal f1 = f2, in steps of 1.5 μs

Graphic representation of the PWVD (Pseudo Wigner-Ville Distribution) of the RF signal

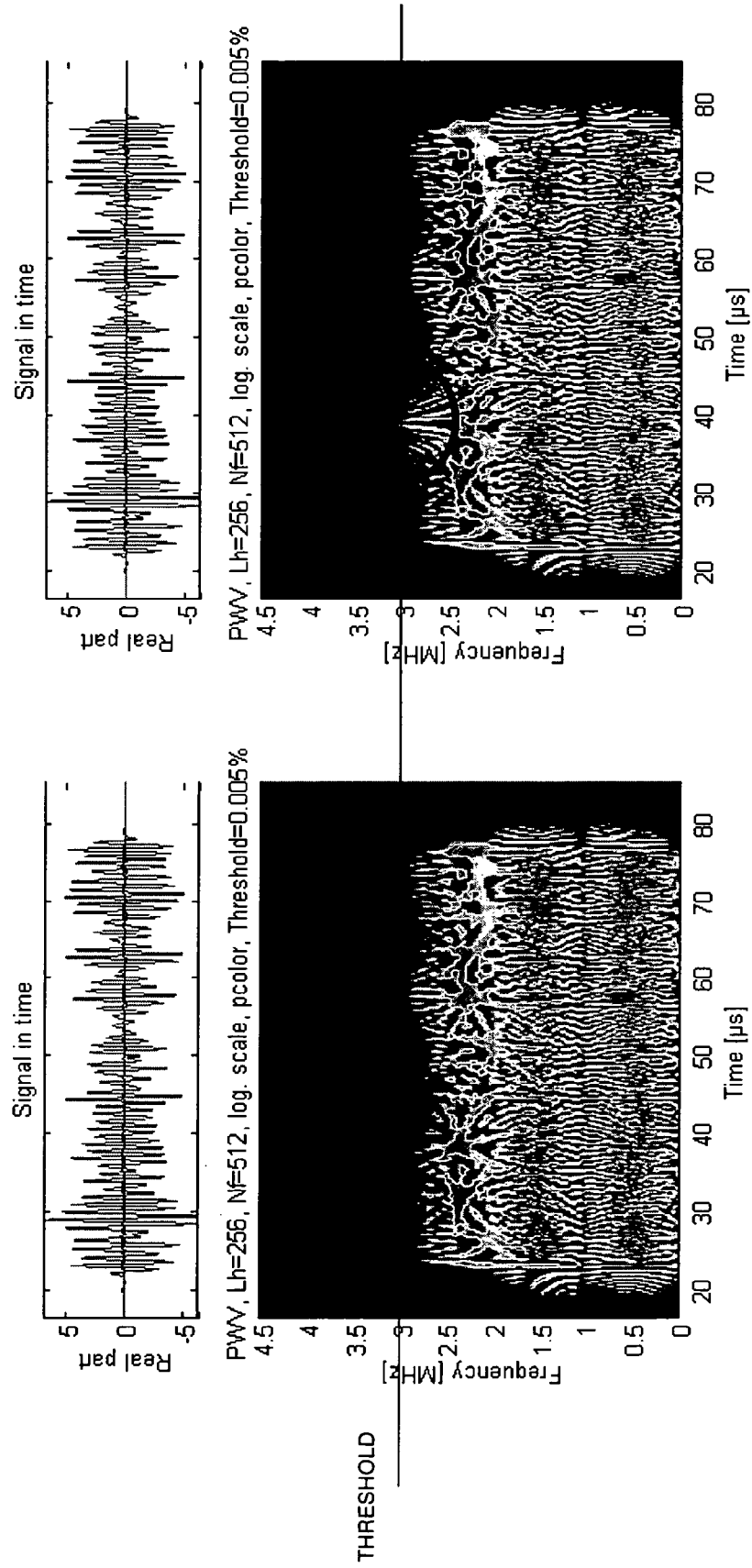

ional steps:
METHOD OF ULTRASONIC DETECTION AND LOCALIZATION OF CONTRAST AGENT MICROBUBBLES AND METHOD FOR LOCAL DRUG ADMINISTRATION BY USING MICROBUBBLE CARRIERS

CROSS-REFERENCES TO RELATED APPLICATIONS

The present application claims the priority benefit of European Patent Application Serial No. 05425222.6, filed Apr. 14, 2005, which is hereby incorporated by reference in its entirety.

BACKGROUND OF THE INVENTION

The invention addresses a method of ultrasonic detection and localization of contrast agent microbubbles, which method comprises the steps of:

scanning an anatomic region in which the presence of contrast agent microbubbles is or may be foreseen, by transmitting one or more ultrasonic pulses at a first predetermined frequency in said anatomic region;

receiving the reflected ultrasonic signals resulting from the transmit pulses;

identifying the presence of reflected ultrasonic signals having at least one second frequency corresponding to at least the second harmonic of the first fundamental frequency of the ultrasonic transmit signals;

associating said reflected ultrasonic signals having at least one second frequency corresponding to at least the second harmonic of the first fundamental frequency of the ultrasonic transmit signals, to contrast agent microbubbles, acting as reflectors;

determining the position of said microbubbles in the anatomic region according to the time localization of the reflected ultrasonic signal or parts of such reflected ultrasonic signal at said at least one second frequency corresponding to the second harmonic of the first fundamental frequency of the ultrasonic transmit pulses within the duration of the whole reflected ultrasonic signal.

The detection of reflected ultrasonic signals in the frequency range corresponding to the second harmonic of the fundamental frequency of one or more ultrasonic transmit pulses is known in the field of ultrasonic imaging as Harmonic Imaging. The use of contrast agents composed of microbubbles, having the function of ultrasonic pulse reflectors is also known. Microbubbles act as non linear reflectors, whereby the reflected ultrasonic wave has a frequency in the frequency range of the second harmonic of the fundamental frequency of the incident ultrasonic wave or pulse. This allows to recognize the presence of contrast agents in an anatomic region under examination. In fact, stationary tissues have reflectors with a mainly linear behavior, whereby the reflected signals have the highest strength in the frequency range corresponding to the fundamental frequency of the excitation pulse/s. Therefore, the non-linear reflector effect of contrast agent microbubbles is typically used to highlight vascular or lymphatic flows which are not sufficiently echogenic and might not be visible by using conventional imaging, or might be covered with signals reflected from the static tissues of the relevant anatomic region, such as the walls of blood or lymphatic vessels or other tissues.

Harmonic Imaging provides excellent results when contrast agents are present in considerable amounts in tissues and particularly in vascular or lymphatic flows.

However, since the so-called echogenic or static tissues have a non linear behavior besides the linear reflection behavior, the signals reflected from such tissues also have spectral components at the second harmonic of the fundamental frequency of the ultrasonic signal transmitted in the relevant anatomic region. Furthermore, non linear reflection responses of such type may be also generated by micromovements of tissues. The components of reflected signals at frequencies other than the fundamental frequency of the signal transmitted in the anatomic region are typically of lower strength than reflected signals generated by contrast agent microbubbles when said contrast agents are present in considerable amounts. This essentially occurs in large vessels.

In small vessels, such as capillaries or the like, the number of contrast agent microbubbles is very small and may even be as small as one microbubble or a small microbubble population, of the order of one or a few tenths of microbubbles.

When a single contrast agent microbubble or a small contrast agent microbubble population is present, the reflected signal particularly at said second harmonic of the fundamental frequency of the transmit pulse, i.e. the signal transmitted to the body being examined, has a very low strength, which is generally lower than the strength of the contribution to said second harmonic frequency generated by the non linear behavior of the static or echogenic tissue.

Therefore, conventional Harmonic Imaging techniques cannot generally detect the presence of a single microbubble or a small microbubble population in the relevant anatomic region, as conventional Harmonic Imaging does not allow to discriminate between said spectral component of the reflected signal, generated by the non linear behavior of the tissue, and the same spectral component generated by the presence of one microbubble or a small microbubble population.

The detection of single bubbles or small contrast agent microbubble populations is important both for checking tissue vascularization conditions, e.g. for angiographic analyses, and for identifying any microvessel or microcapillary feeding tumor tissues, the latter being characterized by an increased vascularization.

In addition to simple contrast agent microbubble detection, information must be also collected about the localization thereof in the relevant anatomic region.

The invention has the object of providing a method as described hereinbefore, which allows detection and localization of single microbubbles or small microbubble populations, i.e. small numbers of contrast agent microbubbles.

The invention achieves the above purposes by providing a method as described above, which has the following additional steps:

reflected signals are projected in one or more multidimensional spaces, to highlight the evolution of the reflected signal spectrum with time and/or the phase relationships between reflected signal components having different frequencies or frequency ranges, particularly the signal components at the fundamental frequency of the transmit pulse/s and at the second harmonic of the transmit pulse/s;

sample reflected ultrasonic signals are detected, by transmitting ultrasonic pulses to known tissue samples containing no single microbubble or small microbubble population and on known tissue samples containing a single bubble or a small bubble population;

the sample reflected ultrasonic signals are projected in the same multidimensional space to highlight the evolution of the reflected signal spectrum with time and/or the phase relationships between the reflected signal components having different frequencies or frequency ranges;

the projections of the sample reflected ultrasonic pulses for simple tissue and tissue having a single microbubble or a small microbubble population in the multidimensional spaces are compared and unique characteristics are defined for said projections for the simple tissue and the tissue having a single microbubble or a small microbubble population;

the projections of reflected signals in multidimensional spaces are analyzed to identify said diversifying characteristics defined on the basis of the comparison between the projections of sample reflected ultrasonic signals in the multidimensional spaces;

a projection of the reflected signal in said multidimensional space being defined as deriving from a single microbubble or a small microbubble population when it has the characteristics of the projection of the sample reflected ultrasonic signal in said multidimensional space relating to the known sample of tissue having a single microbubble or a small microbubble population.

Regarding the localization within the relevant anatomic region, the above method includes the following additional steps:

scanning the relevant anatomic region by transmitting at least one ultrasonic transmit pulse in said region along a plurality of adjacent scan lines;

receiving the reflected signal along each of said scan lines;

analyzing the reflected signal, with the above described method, along each scan line, to identify one signal component deriving from the presence of one microbubble or a small microbubble population and to identify said component of the reflected signal;

determining the position of the microbubble or the small microbubble population along the corresponding scan line according to the time localization of said component within the duration of the reflected signal;

the position of the microbubble or the small microbubble population in the relevant anatomic region being defined by the position of the scan line and the position of the microbubble or the small microbubble population along the scan line.

According to a first embodiment, a first multidimensional projection is provided by analyzing the reflected signal by means of a Higher Order Spectrum, i.e. HOS (see: Mendel J M. *Tutorial on higher-order statistics (spectra) in signal processing and system theory: theoretical results and some applications*. Proc.IEEE, 79, 3, 278-305)

Amongst the various HOS techniques or polyspectra, the reflected signal is represented by a so-called bispectrum.

As explained hereafter, the bispectrum is a representation of the reflected signal in a three-dimensional space, which highlights the phase relationships between the spectral components of the reflected signal. A more detailed description of bispectra, as well as a relevant bibliography, will be provided hereafter.

In this case, the reflected signals at the second harmonic of the transmit pulse/s (which is the typical frequency of reflected signals generated by non linear reflectors such as contrast agent microbubbles) have different characteristics depending on whether said reflected signals are generated by the simple tissue of a relevant anatomic district (i.e. having no contrast agent microbubble), or by the tissue of said anatomic region and by one microbubble or a small microbubble population therein.

The representation of the reflected signal -by a bispectrum allows to detect a single microbubble or a small microbubble population by analyzing the characteristics of the bispectrum of said reflected signal.

A preferred method consists in generating the bispectra of reflected signals of ultrasonic pulses transmitted on known tissue samples having no microbubble and on tissue samples having one microbubble or a small microbubble population, thereby obtaining sample signal bispectra which allow to determine whether one microbubble or a small microbubble population is present by simply comparing the sample signal bispectra and the bispectra of the signal reflected from the relevant anatomic region.

The comparison may be performed by analytical mathematical instruments, which extract the typical characteristics of bispectra indicating the presence of one microbubble or a small microbubble population.

Alternatively, by generating a database of sample signal bispectra, containing the characteristics of the bispectrum of a reflected signal indicating the presence or absence of one microbubble or a small microbubble population in the tissue of the relevant anatomic region, an image, e.g. a digital image, of said bispectra may be generated, and the characteristics of said bispectra may be determined by automatic Image Pattern Recognition systems.

Many Image Pattern Recognition systems are known. Amongst these, some use the predictive functions of artificial neural networks or cellular neural networks. Some of the leading edge systems are disclosed in WO2005/020132A1, U.S. Pat. No 5,140,670, EP 1,345,145.

These HOS and particularly the bispectrum are theoretically deemed to be able to highlight the phase relationships between the spectral components of a signal and to better show the nature of said components possibly as regards the source that generated them.

Since the reflected signal changes with time, the use of a bispectrum, which is a static representation thereof at a certain time requires said signal to be made at least quasi static. Furthermore, in the reflected ultrasonic signal, the time localization of signal components with reference to the duration of the signal is particularly relevant for its being related to the reflector position along the signal propagation axis of the axis of view. In ultrasonic imaging, time is known to be equivalent to a measurement of depth or distance from the receiver, therefore time localization of the reflected signal component indicating the presence of one microbubble or a microbubble population is important because such time localization is also a measurement of the reflector position, i.e. of the microbubble or small microbubble population along the axis of view or scan line or along the reflected signal propagation axis.

For the above reasons, according to the invention, when using polyspectra or HOS the reflected signal is divided into a sequence of segments, so-called blocks, each corresponding to a fraction of the overall duration of the reflected signal.

The blocks may be also defined in such a manner that they can overlap at least partially. Thus, a bispectrum is generated for the part of the reflected signal related to each block, and the characteristics thereof are determined as described above to assess whether one microbubble or a small microbubble population is present or absent therein. Each block, as well as its time location with reference to the overall duration of the signal, acts as a position indicator along the axis of view, or scan or propagation of the reflected signal. Therefore, the time length of each block is a measurement of spatial length and may be changed in such a manner as to have a higher or lower time resolution and, as a result, a higher or lower space resolution.

Therefore, as mentioned above, the receive signal is first divided into a succession of segments, or blocks, having a predetermined time length, and predetermined start and end times with reference to the overall duration of the receive signal and then projected on the multidimensional space, a corresponding bispectrum being generated for each signal block. The bispectrum of each signal block is then subjected to steps of extraction of peculiar characteristics corresponding to the absence or presence of one microbubble or a small microbubble population according to the above steps.

In a variant embodiment of invention, methods of time-frequency analysis of the reflected signal are used to determine whether or not a single microbubble or a small microbubble population is present in the tissue under examination.

Various methods exist of time-frequency analysis of a signal (see: Qian, Shie, Introduction to Time-Frequency and Wavelet Transforms, 1st Ed, Prentice Hall PTR, ISBN: 0130303607). Once again the signal is projected in a multidimensional space.

The signal processed by a time-frequency analysis method is then represented in a diagram in which frequency is plotted against time. Once more, receive signals are used which are generated by ultrasonic pulses transmitted on known tissue samples having no microbubbles or just one microbubble or a small microbubble population and the characteristics of the spectrum representation over time obtained with the time-frequency analysis method are identified for signals received from simple tissue and for signals received from tissue having one microbubble or a small microbubble population respectively.

After identification of the characteristics differentiating the time-frequency analysis representations of the receive signal of the two above mentioned types of receive signals, such characteristics may be extracted by comparison or other techniques such as Image Pattern Recognition techniques, from the receive signal of an anatomic region under examination, exactly as it was provided when bispectra were used as a method of multidimensional projection of the receive signal.

In a first embodiment, the so-called Gabor expansion is used (see: Feichtinger & Strohmer (Eds.), GABOR ANALYSIS & ALGORITHMS: Theory & Applications, Birkhauser/SPRINGER-VERLAG, ISBN: 0817639594; Qian, Shie, Introduction to Time-Frequency and Wavelet Transforms, 1st Ed, Prentice Hall PTR, ISBN: 0130303607).

This specific time-frequency analysis of the receive signal allows to recognize and discriminate the presence of one microbubble or a small microbubble population when the spectral component at the second harmonic of the fundamental frequency of the transmit pulse is dominant with respect to the same spectral component of the receive signal generated by a non linear reflection behavior of the tissues in the anatomic region under examination.

If the signal component generated by the presence of a single microbubble or a small microbubble population has a lower or much lower strength than the same spectral component of the receive signal, generated by non linear reflection from tissues, then Gabor expansion does not allow to detect with a relatively high level of accuracy the presence of one microbubble or a small microbubble population.

Another embodiment of time-frequency analysis is the Wigner-Ville distribution in one of its many variants. (see: 0817639594; Qian, Shie, Introduction to Time-Frequency and Wavelet Transforms, 1st Ed, Prentice Hall PTR, ISBN: 0130303607)

Advantages have particularly resulted from using the so-called Pseudo Wigner-Ville Distribution (PWVD).

This type of time-frequency analysis provides acceptable results even when the spectral component of the receive signal resulting from the single microbubble or a small microbubble population has a lower strength than the same spectral component of the signal resulting from non linear reflection from the tissues of the anatomic region under examination.

As explained below in a more detailed discussion of the mathematical formalism of the PWVD, this type of time-frequency analysis seems to not only highlight the evolution of the received signal with time, but also the phase relationships between the spectral components of the received signal.

When compared with the bispectrum, the PWVD provides automatic segmentation of the receive signal into successive time blocks, and also highlights the phase relationships between the spectral components of the receive signal.

According to an improvement, since the spectral component of the receive signal at the frequency corresponding to the fundamental frequency of the transmit pulse has a considerably higher strength than the spectral components of the receive signal at the second harmonic frequency, regardless of whether these result from one or more contrast agent microbubbles, advantages are obtained by providing an additional step before projecting the receive signal in the multidimensional space and/or dividing it into a succession of time blocks. This additional step consists in subjecting the receive signal to filtering or processing to remove the spectral component thereof in the range of the fundamental frequency of the transmit pulse.

The additional filtering step allows to reduce the differences in strength between the remaining signal components at the second or higher harmonic frequency and thereby improves prediction accuracy, i.e. allows to safely determine whether a single microbubble or a small microbubble population is present or not. As stated above, the determination of the presence and position of a single contrast agent microbubble or a small contrast agent microbubble population is considerably important, not only for checking for small vessels but also in combination with new types of contrast agents, in which microbubbles are designed to only bond to target regions or tissue types. In this case, microbubbles have such a chemical and molecular structure as to bond to a desired tissue type.

For instance, in microvessel density measurement, which may be of help in evaluating the presence and the evolution stage of prostate cancer, microbubbles may have bioconjugate ligands which are capable of bonding to the endothelium of the new vessels associated to the vascularization caused by the onset of such tumor. Contrast agent microbubbles having structures with bioconjugate ligands capable of selectively bonding to specific types of derived tissues are known, for instance, from Dayton P., Ferrara K., "Targeted Imaging Using Ultrasound" Journal of Magnetic Resonance Imaging, vol. 16, pp. 362-377, 2002; Hall C. S., Marsh J. N., Scott M. J., Gaffney P. J., et al., "Temperature dependance of ultrasonic enhancement with a site-targeted contrast agent", Journal of Acoustic Society of America, vol. 110, issue 3, pp. 1677-1684, September 2001; Hughes M. S.,m Lanza G. M., Marsh J. N. Wickline S. A., "Targeted ultrasonic contrast agents for molecular imaging therapy: a brief review" Medicamundi, vol. 47, no.1, pp. 66-73, April 2003) and are known as targeted microbubbles. In these cases, safe detection of single microbubbles or small microbubble populations is highly important.

The method of detecting the presence and position of single contrast agent microbubbles or small microbubble populations is even more important when said method is provided in combination with said microbubbles having a structure capable of selectively bonding to certain predetermined types of tissues, and being further able to carry medicaments therein. In this case, microbubbles reach the predetermined tissues and bond to them and, once they are detected, they may be caused to break by using ultrasonic transmit pulses having such a strength as to generate high acoustic pressures. The destruction of microbubbles allows local drug delivery to the predetermined tissues.

Therefore, the method of detecting single microbubbles or small microbubble populations is provided, according to this invention, in combination with contrast agents whose microbubbles contain bioconjugate ligands capable of bonding to predetermined tissue types.

Also, the method of this invention is provided in combination with microbubbles containing bioconjugate ligands with drugs therein.

Therefore, the invention relates to a method for local drug administration to predetermined tissues, which provides microbubbles having a structure with bioconjugate ligands capable of selectively bonding to predetermined tissue types, and which microbubbles carry predetermnined doses of a drug therein whereas detection of microbubbles in predetermined tissues is effected by using the method of detection of single microbubbles or small microbubble populations according to this invention and according to any one of the variants as described above whereas, once the presence and/or position of single microbubbles or a small microbubble population are detected, one or more transmit pulses are transmitted, which have such a strength as to generate a sufficient acoustic pressure to destroy (rupture) said microbubbles.

Further improvements of the inventive method will form the subject of the dependent claims.

BRIEF SUMMARY OF THE INVENTION

A method of ultrasonic detection and localization of contrast agent microbubbles is disclosed, characterized in that the decision as to whether or not the received ultrasonic signals indicate the presence of a single microbubble or a small microbubble population is made by analyzing the projections of the spectra of the received ultrasonic signals in multidimensional spaces, and by comparing such projections with the projections in the multidimensional spaces of sample control signals corresponding to known conditions of presence and/or absence of single microbubbles and/or small microbubble populations.

One object of the present invention is to provide an improved method of ultrasonic detection and localization of contrast agent microbubbles.

Related objects and advantages of the present invention will be apparent from the following description.

BRIEF DESCRIPTION OF THE SEVERAL VIEWS OF THE DRAWINGS

FIGS. 17, 18 and 19 respectively show an image of a bispectrum and the quadrant thereof which is repeated twelve times in the whole image delimited by lines L1 and L2.

FIGS. 18 and 19 show the evolution of the bispectrum with time along the diagonal, i.e. line L1, in time steps of 1.5 microseconds respectively for the receive signal resulting from simple tissue and for the receive signal resulting from tissue containing a small bubble population at a depth approximately corresponding to the time of 35 microseconds.

FIGS. 25 and 26 are like FIGS. 23 and 24, relating to another case.

FIG. 27 is a simplified flow chart which shows in greater detail the steps of the method in which the position of the detected single microbubbles or small microbubble populations are displayed in a conventional image, e.g. a B-Mode image or the like.

DETAILED DESCRIPTION OF THE INVENTION

Figure 1:
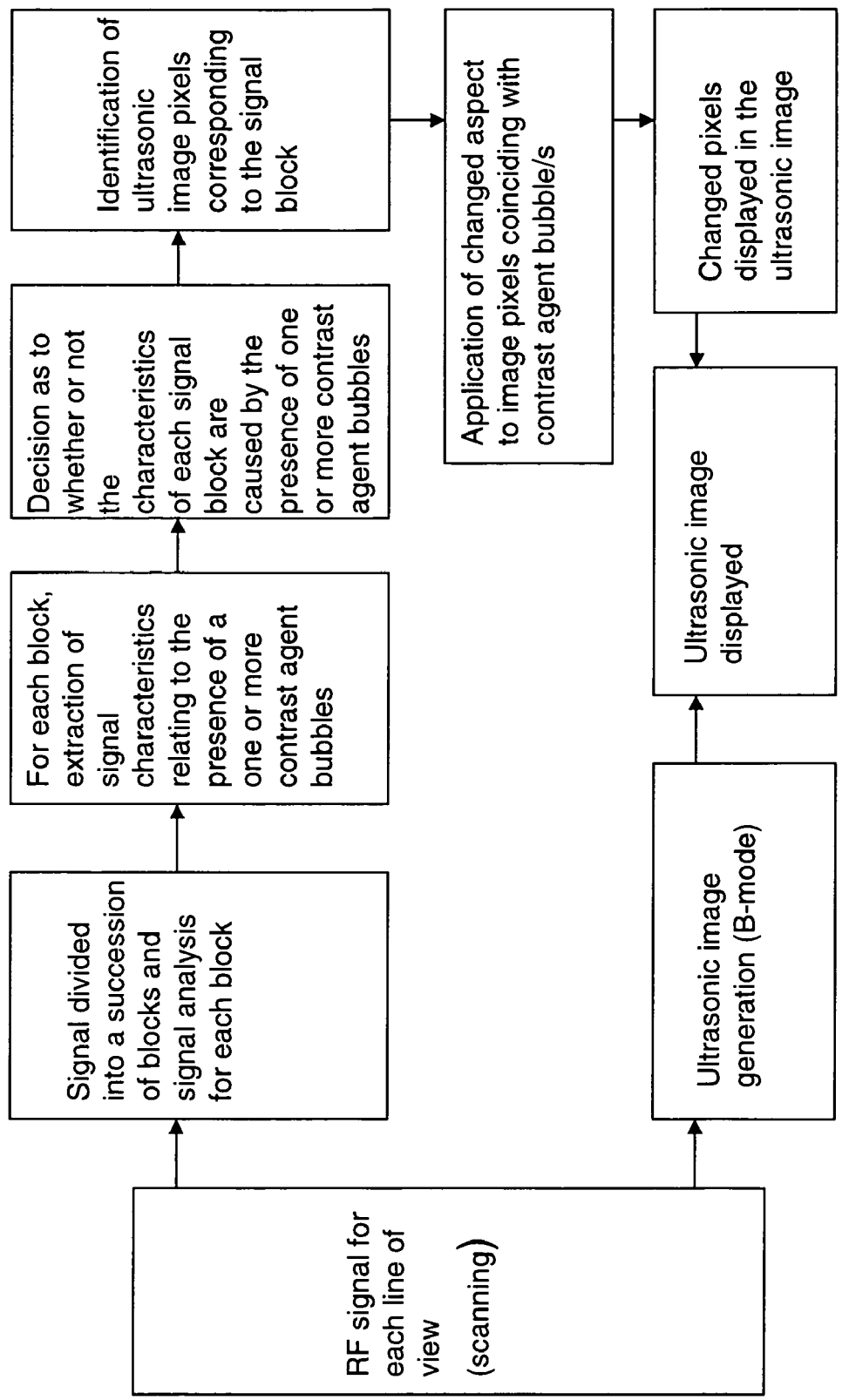
FIG. 1 shows a flow chart that generally summarizes the steps of the method according to the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In conventional ultrasonic imaging, a probe is used having arrays of piezoelectric transducers which turn an oscillatory electric signal into a corresponding acoustic, particularly ultrasonic signal. An anatomic region under examination is scanned for ultrasonic imaging along scan planes corresponding to slices of the relevant anatomic region. In order to perform scanning along a scan plane, a succession of pulses is transmitted from the probe toward the relevant anatomic region, along adjacent scan lines which subtend the desired scan plane. The scan pulse transmitted from the probe is composed of the contributions of pulses transmitted from each of the ultrasonic transducers of the probe and such transducer contributions to the transmit pulse are focused along the individual scan lines by applying. transducer excitation delays to the transmission of the corresponding ultrasonic pulse. Focusing of scan pulses during transmission is known in the field of ultrasonic imaging as beamforming.

The transmit pulses focused along each scan line are reflected from the material along the line of view in the anatomic region under examination and the reflected ultrasonic pulses are detected and turned into electric receive signals by piezoelectric transducers, which are generally the transmitting transducers themselves. The contributions to the reflected signal provided by the reflectors along the scan line are selected by receive focusing which is also effected by applying receive time windows with corresponding delays for each piezoelectric transducer. This technique is also known, with the name of receive beamforming. Both transmit beamforming and receive beamforming and the associated determination of transmit delays and receive delays for each piezoelectric transducer are determined according to acoustic wave propagation rules and to the propagation speed thereof with well-known precise functions.

The ultrasonic receive signals along each adjacent scan line form the image data of an ultrasonic two-dimensional image of the relevant anatomic region along a scan line that contains said scan lines. The penetration depth of the transmit signal, therefore the reflection depth of the receive signals is proportional to the signal propagation time.

The receive signals along a scan line are uniquely related to a precise relative position and may be therefore converted into image data to be displayed with different intensities and/or colors in a two-dimensional digital image.

Conventional ultrasonic images, for instance so-called B-Mode images, are generally grey-scale images. The higher or lower strength of the receive signal corresponding to each pixel is highlighted in the image in the form of a corresponding degree of the grey scale and, as a rule, the brighter an image pixel the higher the intensity of the corresponding receive signal, whereas for low intensities, the corresponding pixel of the digital image has an accordingly dimmer aspect.

Since vascular or lymphatic flows generally have the characteristic of being bad reflectors and the signal reflected therefrom has a much lower strength than that reflected from static tissues of the anatomic region, vascular or lymphatic flows cannot be detected by conventional ultrasonic imaging.

Vascular or lymphatic flows may be ultrasonically imaged by using a known technique which includes the injection of contrast agents in the anatomic region. Such contrast agents are carried by said flows and their structure allows them to act as non linear reflectors. Typically, these contrast agents are made of microbubbles, whose structure allows them to reflect an impinging incident ultrasonic pulse at a different frequency from the incident pulse itself. Particularly, the non linear behavior is calibrated in such a manner that the reflected signal deriving from a pulse impinging upon a contrast agent microbubble has a frequency equal to or in a range of frequencies essentially centered on the second harmonic of the fundamental frequency of the incident pulse.

Since the spectral contributions of tissues containing no contrast agents in the relevant anatomic region and stationary tissues in general is at the same frequency as or in the range of frequencies centered on the fundamental frequency of the incident pulse, the receive signals resulting from contrast agent microbubbles may be recognized or discriminated thanks to the fast that they form a different spectral component of the receive signal, even though the strength of the receive signal component at the frequency or in the range of frequencies centered on the fundamental frequency of incident pulses is much higher than the strength of the receive signal component at the frequency or in the range of frequencies centered on the second harmonic of the fundamental frequency of incident pulses.

Nevertheless, regarding vascular or lymphatic flows through microcapillaries, the number of contrast agent microbubbles in said microcapillaries may be as small as one microbubble or a small microbubble population.

In these conditions, the strength of the receive signal component resulting from microbubbles is very low and even lower than the strength of the receive signal component in the same frequency range, resulting from a non linear behavior of static tissue reflectors in the relevant anatomic region. Therefore, conventional Harmonic Imaging cannot directly detect single microbubbles or small microbubble populations.

Referring to FIG. 1, the method of the invention provides processing of ultrasonic receive signals along each scan line in two parallel modes.

For the sake of simplicity, the examples of the figures relate to a single scan line, a plane being scanned by successive scanning operations along a plurality of adjacent scan lines subtending said scan plane.

Referring to FIG. 1, in the most general form of the method of this invention the Radio Frequency (RF) signal obtained in parallel along each scan line with a known conventional ultrasonic imaging technique, for instance with the known B-mode imaging methods resulting in two-dimensional, generally grey scale digital images is provided to an image data generation channel. The RF receive signal is provided in parallel to a processing chain which segments said signal into a succession of time blocks and then analyzes the receive signal segment for each block, whereby any receive signal component resulting from a single microbubble and/or a small microbubble population is detected. Thanks to the analysis of each signal segment of each block, the receive signal, i.e. each segment thereof, is subjected to extraction of the characteristics associated to the presence of a single microbubble or a small microbubble population. In the next step, based on the characteristics extracted from the signal segments of the individual blocks, a decision is made as to whether said characteristics denote or not the presence of a microbubble or a small microbubble population. (See FIGS. 3 and 4.) Depending on the scan line associated to the receive signal and on the time block whereto the signal segments belong, whose characteristics have denoted the presence of a single microbubble or a small microbubble population, the B-mode digital image pixel/s may be determined which coincide with the detected single microbubble or with the small microbubble population. Therefore, these pixels are highlighted in the B-mode grey scale image, for instance by an aspect change, e.g. assignment of a predetermined color.

Parallel processing allows optimal manipulation of the RF receive signal, on the one hand to generate the three-dimensional image and on the other hand to identify the presence of single microbubbles or small microbubble populations.

Furthermore, display modes allow a visual identification of the position of said microbubbles detected in the tissues of the relevant anatomic region.

Figure 2:
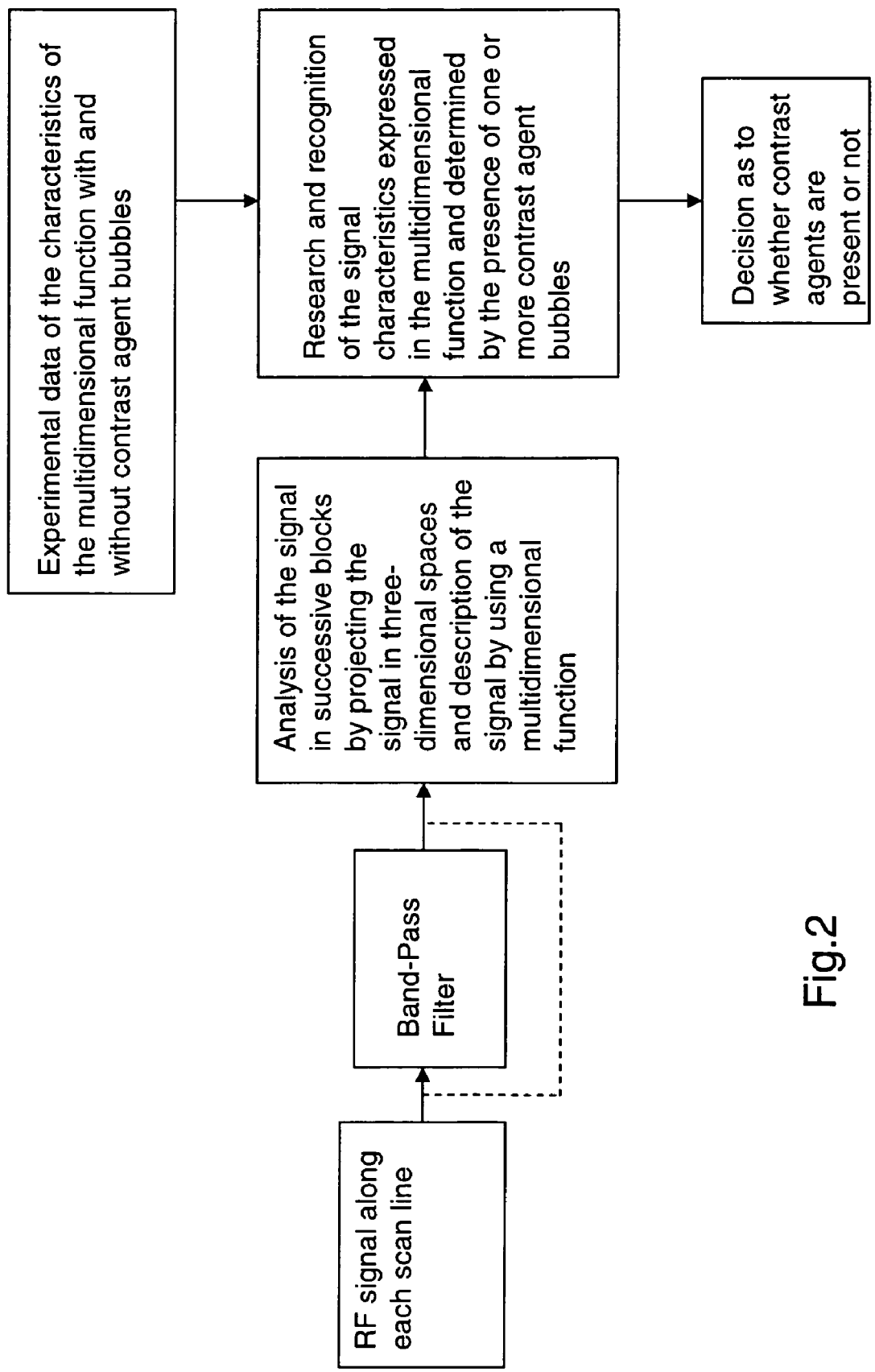
FIG. 2 also shows a flow chart, which further includes the steps of the method for detection of single microbubbles or small microbubble populations according to this invention.

FIG. 2 shows in greater detail the methods of analysis of the RF signal for determining the components that denote the presence of one microbubble or a small microbubble population along the corresponding scan line.

An advantageous method of analysis of the RF receive signal consists in projecting the segment signal of each time block in a multidimensional space.

An appropriate selection among the existing projections in multidimensional spaces allows to highlight the characteristics of the RF receive signal associated to the presence of single microbubbles or small microbubble populations.

The characteristics of said projections that are uniquely related to the absence of microbubbles or to the presence of single microbubbles or small microbubble populations may be recognized by determining the projections of receive signals in the selected multidimensional space, which receive signals result from known tissue samples having or lacking single microbubbles or small microbubble populations respectively.

The information obtained from the projections of receive signals resulting from these samples is used as a reference to identify the characteristics of said projections of receive signals which uniquely denote the presence or absence of single microbubbles or small microbubble populations. The signals received from the relevant anatomic region are checked for said characteristics that were identified by the sample receive signals and, depending on whether said characteristics are detected or not, the presence or absence of single microbubbles or small microbubble populations is determined.

The receive signal characteristics that typically denote the presence or absence of single microbubbles or small microbubble populations as defined above may be extracted by using numeric computation methods.

Alternatively, graphic representations may be generated in the form of digital images of said multidimensional projections of sample receive signals, to identify the peculiar characteristics of said digital images, that are uniquely related to the absence or presence of single microbubbles or small microbubble populations. Here, the peculiar characteristics that were previously identified by using sample receive signals are advantageously extracted from the receive signals reflected from the anatomic region under examination by further generating graphic representations in the form of digital images of the multidimensional projections of the receive signals reflected from said anatomic region under examination and by analyzing said digital images with known automatic image recognition and interpretation algorithms, e.g. by using known Image Pattern Recognition techniques.

Databases of sample receive signals may be also generated, for training predictive algorithms, such as artificial neural networks or the like, which are image data inputs of digital images representing the multidimensional projections of receive signals.

Figure 4:
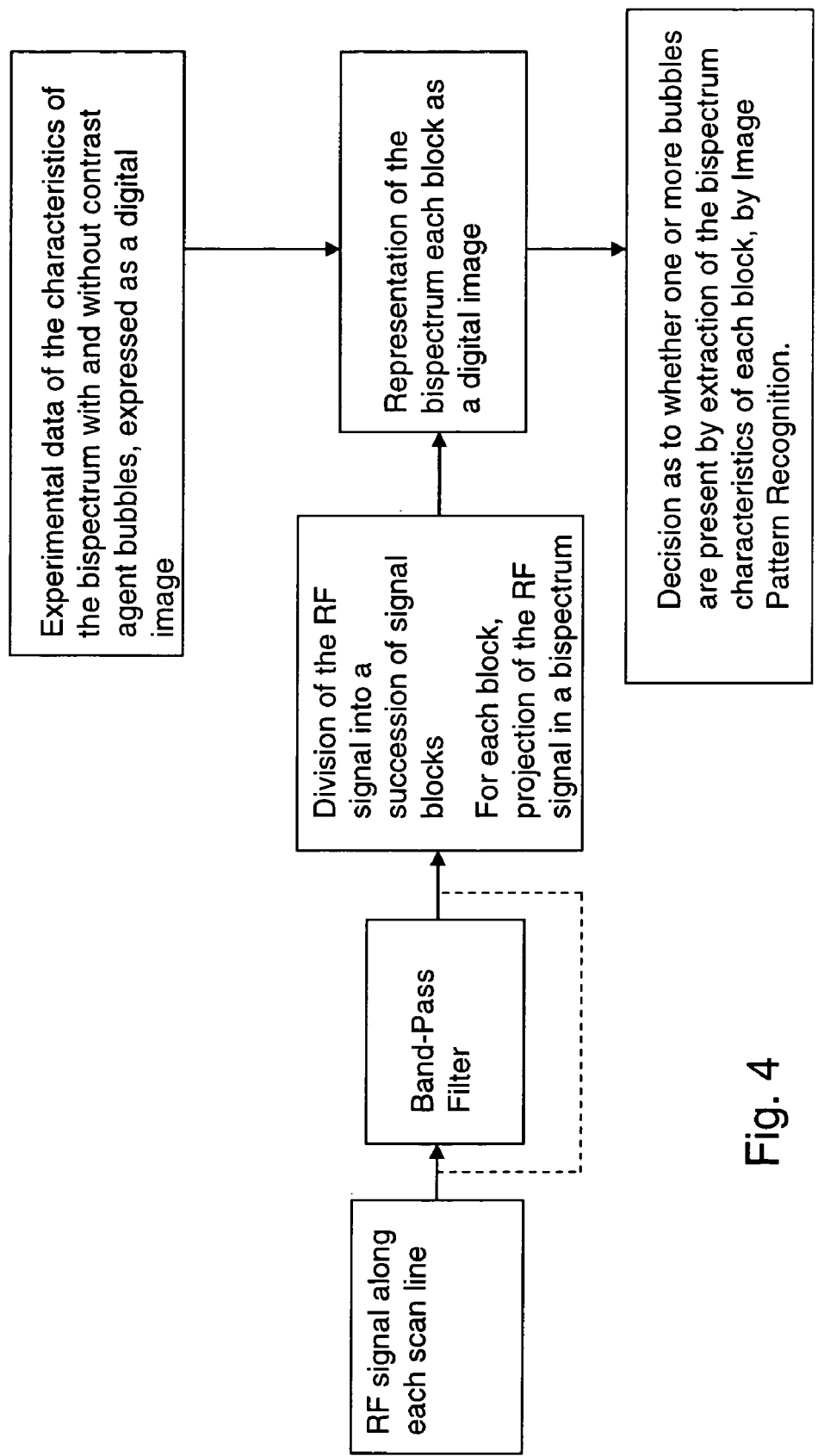
FIG. 4 shows a method for extraction of bispectrum characteristics which includes comparison of digital images of the receive signal bispectrum of the anatomic region under examination with those of sample receive signals.

Still referring to FIG. 4, a specific multidimensional projection of receive signals is shown, which is known as bispectrum.

The bispectrum theory is known and described in greater detail, for example, in Mendel J M. *Tutorial on higher-order statistics (spectra) in signal processing and system theory: theoretical results and some applications*. Proc.IEEE, 79, 3, 278-305.

Starting from the classical spectral estimation, in which the Power Density Spectrum of a stationary stochastic process is defined as a Fourier Transform (FT) of the autocorrelation function:

$$P_{xx}(f) = FT\{R_{xx}(\tau)\}$$

$$R_{xx}(\tau) = E\{x(t)x(t+\tau)\}$$

This corresponds to the mean of the square wave Fourier transform:

$$P_{xx}(f) = E\{X(f)X^*(f)\} = E\{|X(f)|^2\}$$

$$X(f) = FT\{x(t)\}$$

For a zero mean process, autocorrelation equals to the second order cumulant of the signal.

Higher order cumulants may be also provided:

$$C_{2x}(\tau) = R_{xx}(\tau) = E\{x(t)x(t+\tau)\}, \bar{x}=0$$

$$C_{3x}(\tau,\nu) = E\{x(t)x(t+\tau)x(t+\xi)\}, \bar{x}=0$$

$$C_{4x}(\tau,\nu,\xi) = E\{x(t)x(t+\tau)x(t+\nu)x(t+\xi)\}, \bar{x}=0$$

In wider terms, the bispectrum is the two-dimensional Fourier Transform (FT2D) of the third order cumulant (tricorrelation).

Therefore, the bispectrum is defined as follows:

$$P_{3x}(f_1, f_2) = FT_{2D}\{C_{3x}(\tau,\nu)\}$$

Like for the spectrum, this corresponds to the mean of an appropriate product of Fourier transforms of the signal:

$$P_{3x}(f_1, f_2) = E\{X(f_1)X(f_2)X^*(f_1+f_2)\}$$

While in conventional spectral estimation, the FT phase is removed and the power spectrum only takes positive values and is an even spectrum.

In the bispectrum, the FT phase is NOT removed.

The bispectrum has complex values and is symmetric, as the plane (f1, f2) repeats the information contained in a particular base triangle 12 times.

The conventional non parametric spectral estimation of stochastic processes (whereof a restricted number of samples is known) provides two alternatives:

Correlogram (indirect estimation): autocorrelation is estimated and the Fourier Transform thereof is determined Periodogram (direct estimation): the mean of square wave Fourier Transforms for successive signal blocks is determined.

Similarly, the estimation of the bispectrum may also be a direct or indirect estimation.

Like the periodogram in the conventional spectrum, direct estimation of the bispectrum uses the equation that links the bispectrum with the signal FT $$P_{3x}(f_1, f_2) = E\{X(f_1)X(f_2)X^*(f_1+f_2)\}$$

In order to determine the mean, the signal is segmented into partly superposed blocks, and for each of them the FT is determined, as well as the product according to the above equation. In the end, the results of the products are averaged. The bispectrum so obtained is also known as biperiodogram.

In order to obtain a consistent estimation, a smoothing filter on the plane (f1, f2) is applied, i.e. the Rao-Gabr optimal window.

In indirect estimation, like the correlogram for the conventional spectrum, the third order cumulant is estimated to obtain the bispectrum through the FT2D.

$$C_{3x}(\tau,\nu)=E\{x(t)x(t+\tau)x(t+\nu)\}, \text{ i } \bar{x}=0$$

$$P_{3x}(f_1,f_2)=FT_{2D}\{C_{3x}(\tau,\nu)\}$$

The signal is segmented into partly superposed blocks, and for each of them the third order cumulant is estimated, a maximum limit being established for $\tau$ and $\nu$.

In the end, the cumulants of the blocks are averaged and the result is smoothed by windowing (e.g. Parzen windowing), to obtain a consistent estimation.

The FT2D of the windowed cumulant produces the bispectrum.

The methods of direct or indirect estimation of the bispectrum may be alternatively used and both provide useful results.

Signals having superposed spectra may be separated by using bispectrum-based analysis. The bispectrum projects the signal onto a bifrequency plane, whereas the conventional spectrum is situated along the bispectrum axes.

The bispectrum allows to analyze any phase relationships existing between the various frequency components whereof the spectrum only denotes the presence.

The non-linearities cause phase coupling between the harmonics induced thereby. In addition to non-linearity detection, the bispectrum allows to differentiate non-linearities having different natures and proportional entities.

Figure 3:
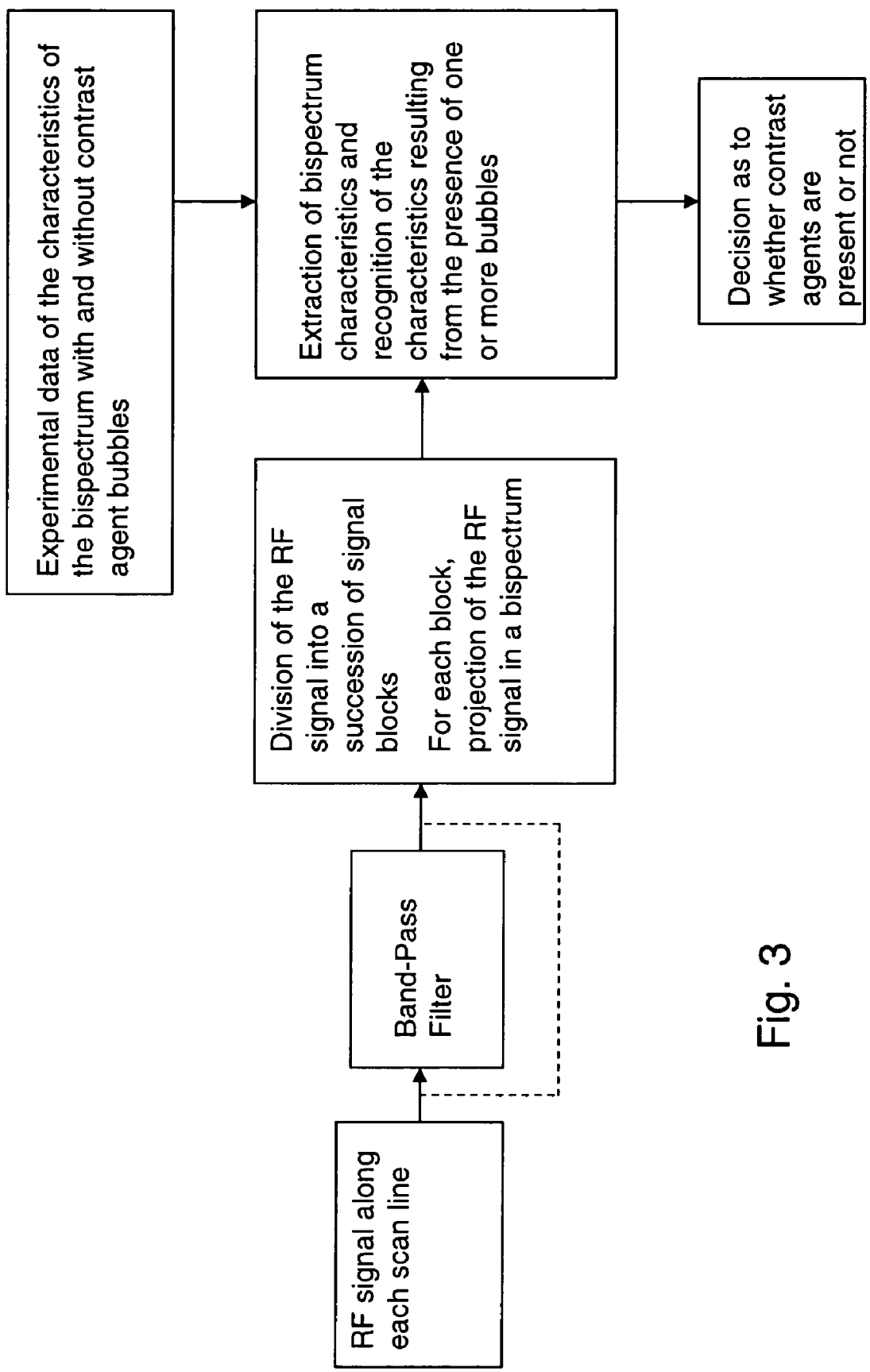
FIG. 3 shows the flow chart of FIG. 2, in which the so-called bispectrum is used as a multidimensional projection of the receive signal.

It shall be noted that in an improvement, as shown in the flow charts of FIGS. 2 to 4, provides a step in which the RF receive signal is filtered by a Band-Pass Filter. This step is optional, as shown by the by-pass dashed arrow, however it may be useful for a more accurate and reliable detection of single bubbles or small bubble populations.

By comparing the strengths of the receive signal resulting from simple tissue and the receive signal resulting from one or a small population of contrast agent microbubbles, the energy ratio of the receive signal component associated to that one or small population of microbubbles to the component associated to simple tissue appears to be of −25 to −35 dB, considering the whole spectral range including both the frequency corresponding to the fundamental frequency of the transmit pulse and the frequency corresponding to the second harmonic frequency and/or the third harmonic of said fundamental frequency.

By substantially limiting the spectral range to a window comprising frequencies of the order of the second and/or third harmonic and by removing the spectral component of the receive signal in the range of the fundamental frequency of transmit pulses, such ratio is generally reduced to about −10 dB. The removal of the receive signal component in the frequency-range corresponding to the fundamental frequency of the transmit pulse does not involve removal of the information useful for detection of single microbubbles or small microbubble populations and further reduces the energy difference between the non linear components of the receive signal, resulting from non linear behavior of tissues and from the presence of microbubbles respectively.

Figure 5:
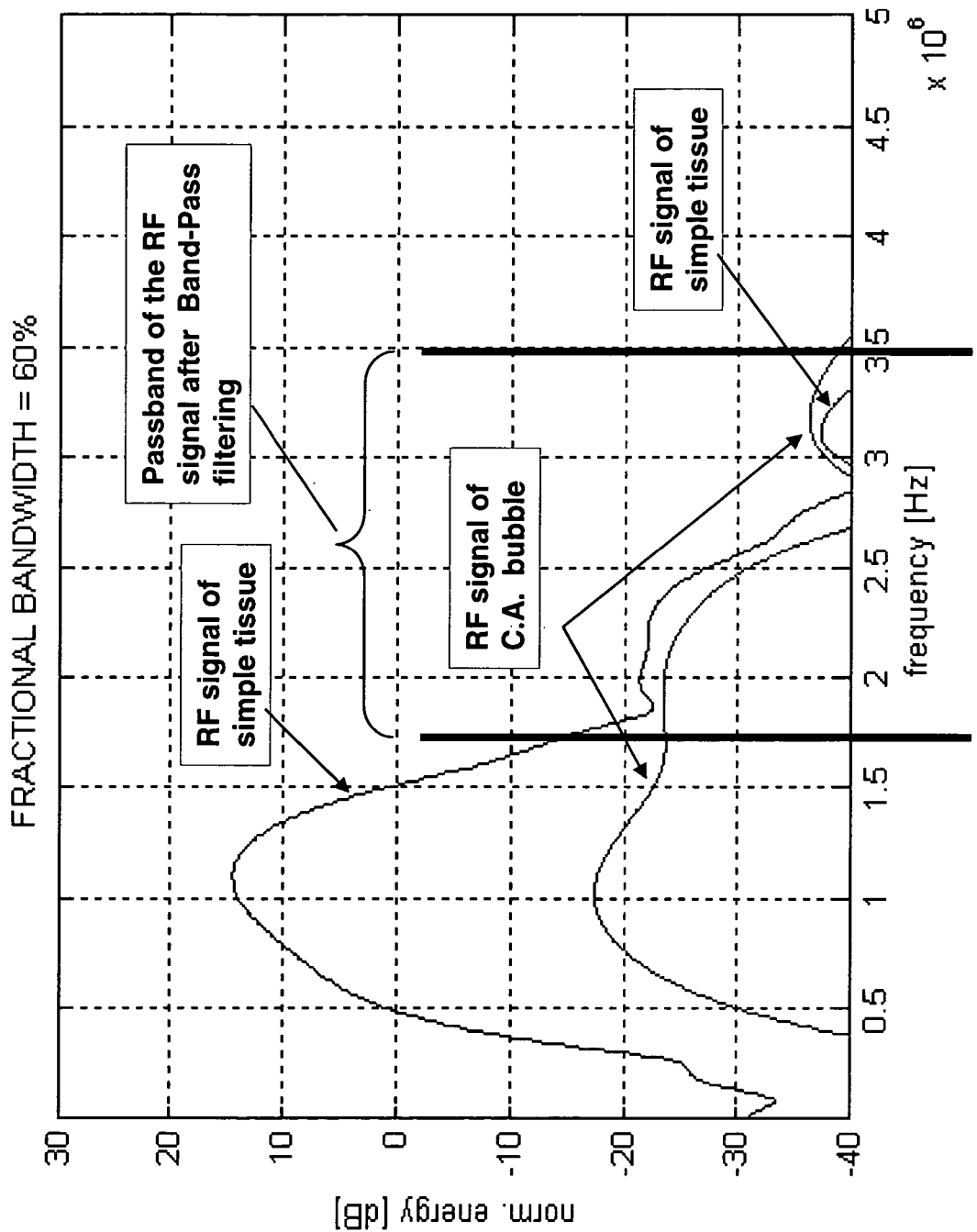
FIG. 5 shows the spectrum of a typical receive signal resulting from simple tissue against the spectrum resulting from the presence of one microbubble or a small microbubble population.
Figure 6:
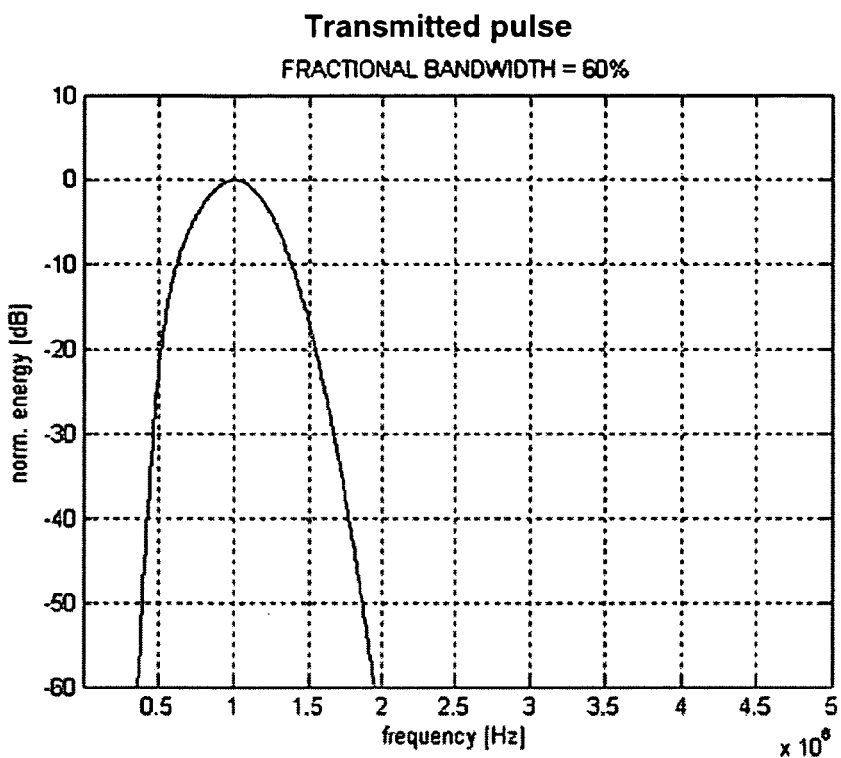
FIGS. 6 and 7 shows the spectrum of a transmit pulse and the associated bispectrum respectively.
Figure 7:
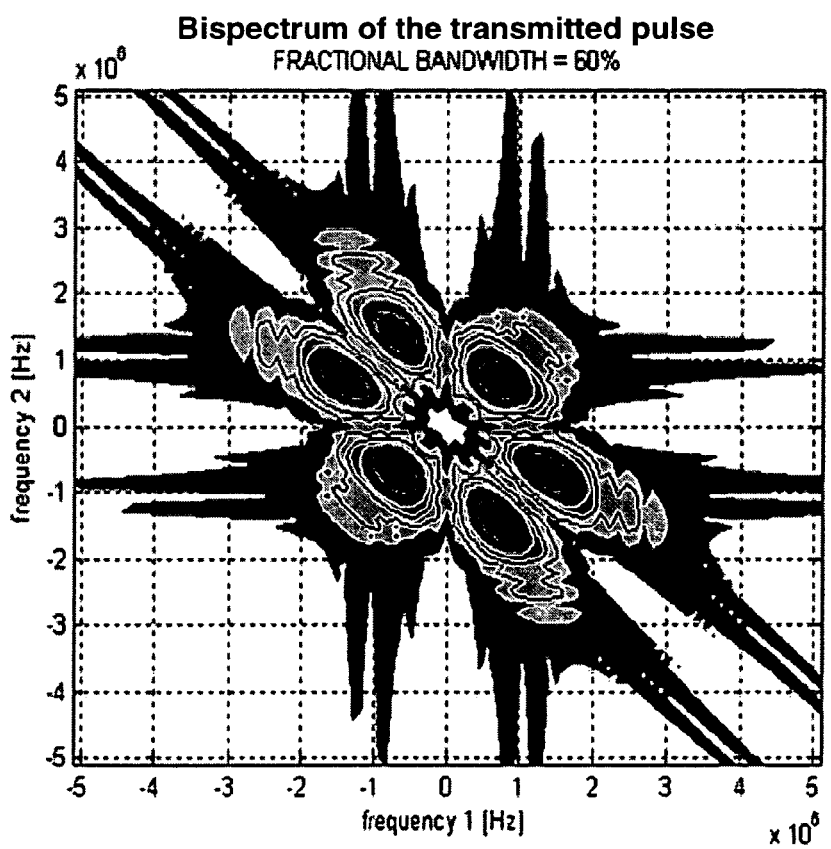
Figure 8:
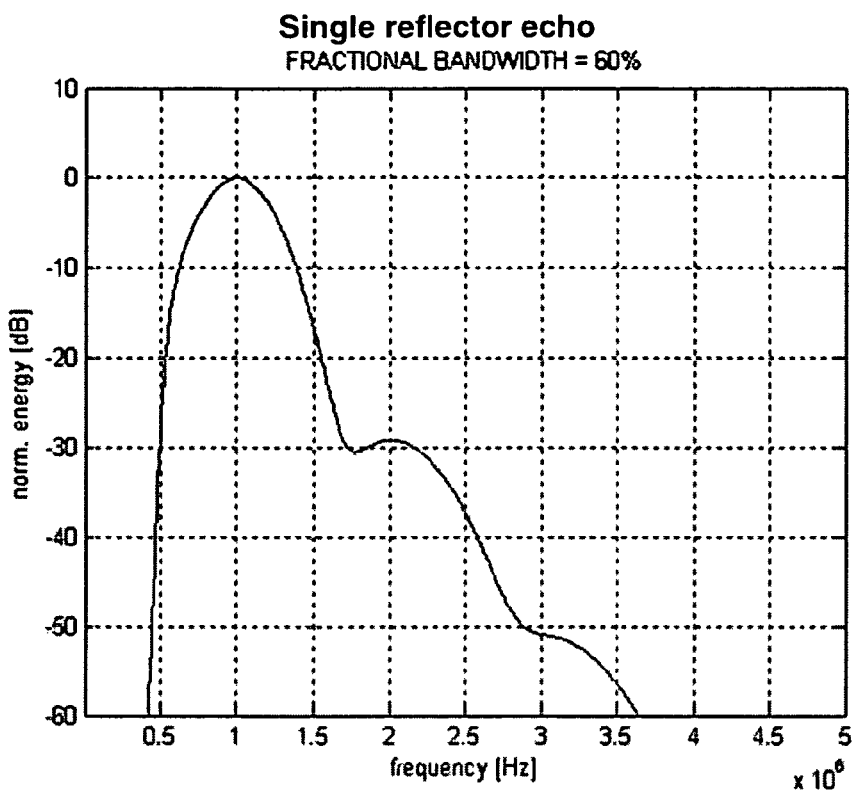
FIGS. 8 and 9 respectively show the spectrum and the bispectrum of the receive signal reflected from a single reflector having a linear and non linear behavior like the reflectors in the tissues of an anatomic district.
Figure 9:
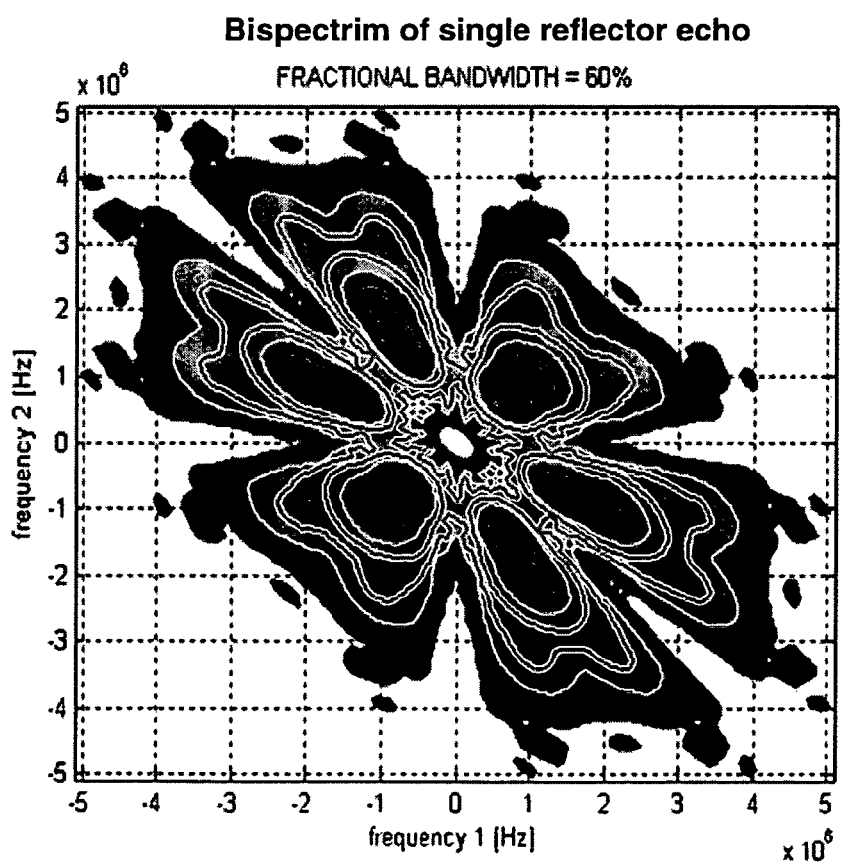
Figure 10:
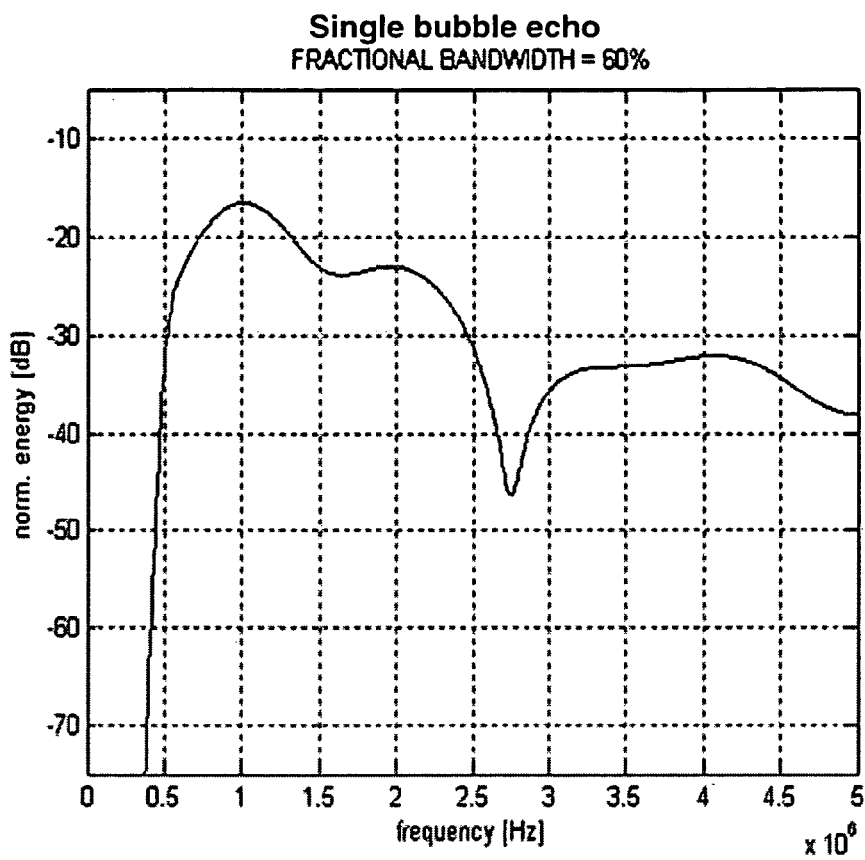
FIGS. 10 and 11 respectively show, like the previous figures, the spectrum and bispectrum of the receive signal reflected from a single contrast agent microbubble.
Figure 11:
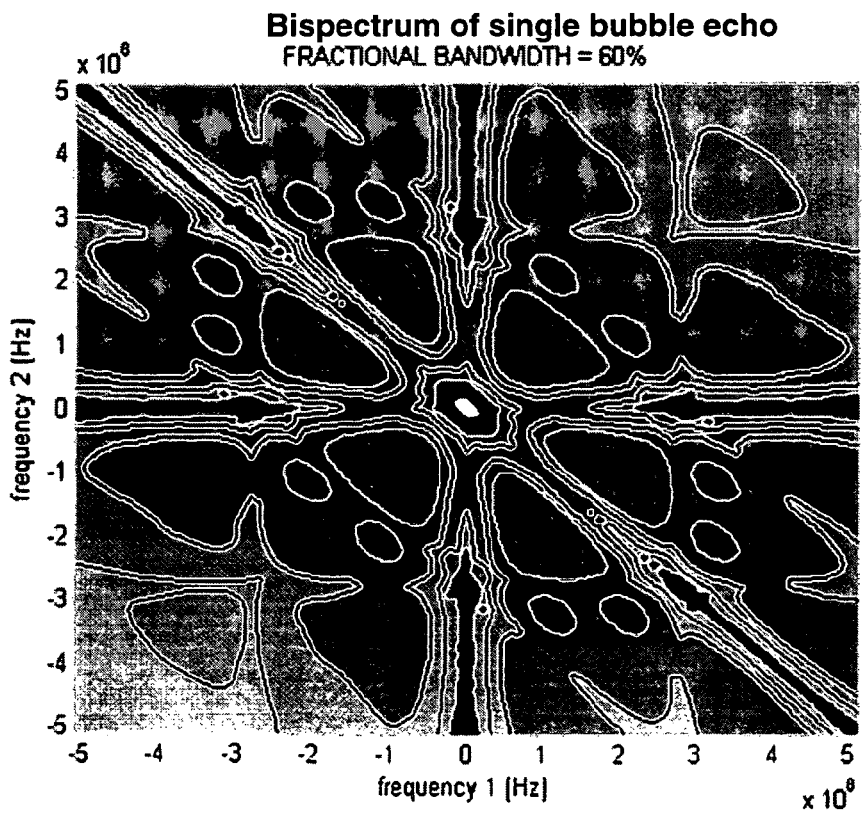

FIG. 5 shows the energy spectrum of the receive signal, resulting from simple tissue and from the presence of one microbubble. FIG. 5 clearly shows the energy relationships between these signals. The figure also highlights the part of the signal that is allowed to pass by the Band Pass Filter.

The next pairs of FIGS. 6 and 7, 8 and 9 and 10 and 11, respectively show the spectral energy distribution and the graphic representation of the corresponding bispectrum of a transmit pulse and the reflected signal resulting from the reflection of said transmit pulse from a simple tissue reflector and from a single microbubble reflector respectively.

The figures clearly show the differences between these signals in the graphic representation of the bispectrum thereof.

Figure 12:
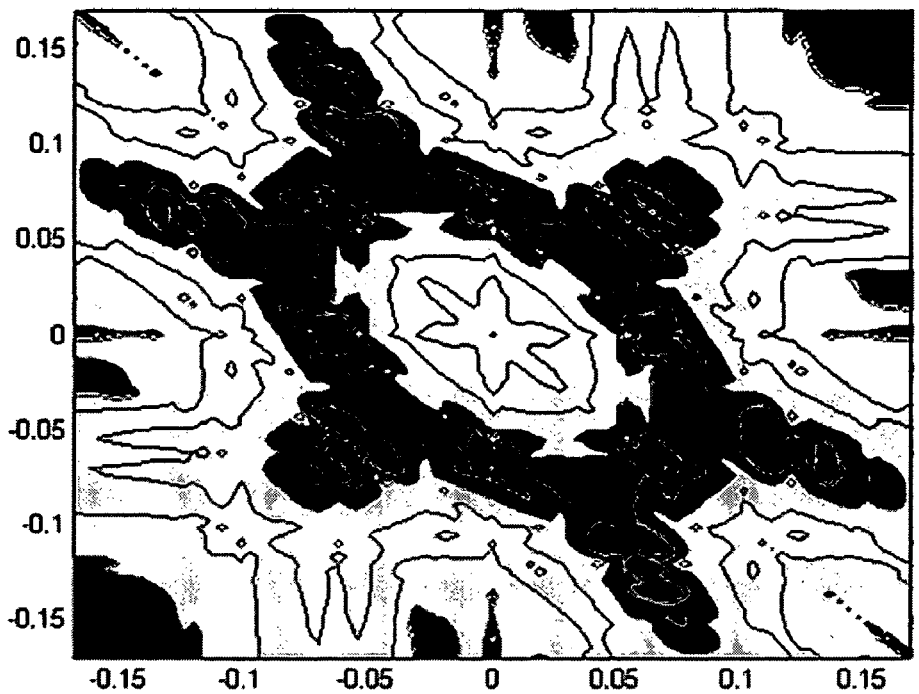
FIGS. 12 and 13 respectively show the bispectrum of the reflected signal resulting from the simple tissue of an anatomic region and the bispectrum of the reflected signal resulting from the combined action of the tissue of an anatomic region and a single contrast agent microbubble.
Figure 13:
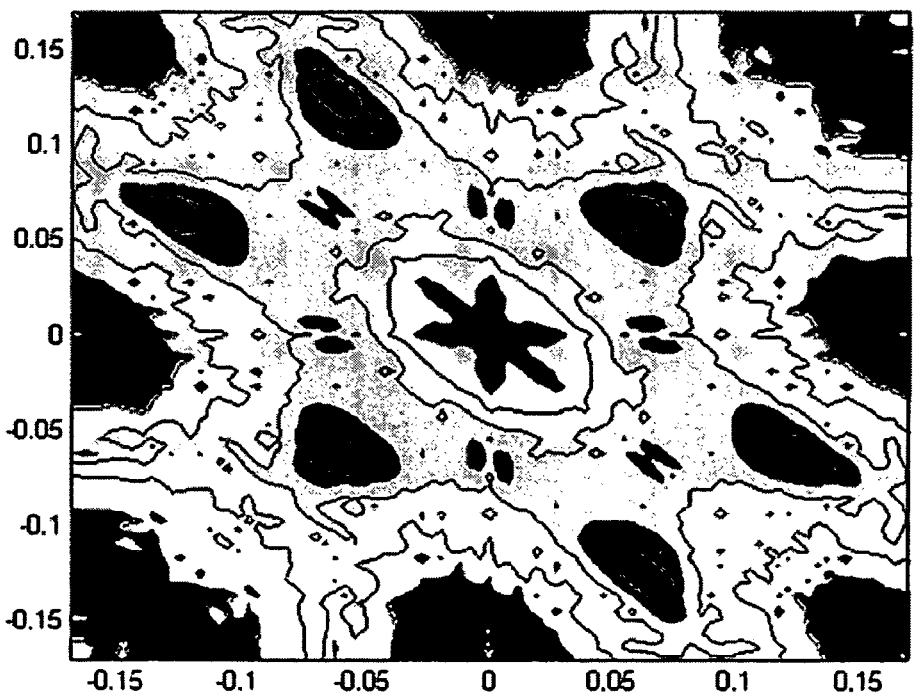

FIGS. 12 and 13 are respective graphic representations of the bispectrum of the receive signal generated by the simple tissue of an anatomic region under examination and the bispectrum generated by tissue containing one microbubble. The figures clearly show that differences exist between the two bispectra and that, by representing the receive signal by a bispectrum, the presence or absence of any single microbubble may be highlighted.

Regarding the graphic representations of bispectra, these are three-dimensional diagrams in which the signal strength or energy is shown with respect to a bifrequency plane, i.e. defined by two axes that define two different frequencies. Obviously the bispectrum images in the above figures are images of the bifrequency plane, whereas the third dimension, i.e. signal energy is denoted by a gray scale or false colors.

As previously stated, the bispectrum of receive signals may be estimated by numeric methods by using direct and indirect estimation means, to identify whether such signals contain or not characteristics indicative of the presence of one microbubble.

Nevertheless, in order to determine the peculiar characteristics of tissue bispectra containing a single microbubble, a certain number of bispectra of sample receive signals must be generated, by using known tissue samples both lacking microbubbles and having one microbubble or a small microbubble population.

From such database of sample receive signals and sample bispectra thereof, peculiar bispectra characteristics associated to the absence or presence o a single microbubble in a tissue may be identified.

Since the differences between the conditions of presence and absence of a single microbubble are apparent even when bispectra are represented in the form of digital images, the bispectrum of a receive signal obtained from an anatomic region under examination may be compared with the sample bispectra to check for resemblance of the digital image representing the bispectrum of said receive signal to the digital images representing the bispectra of sample receive signals.

Various comparison and image processing techniques may be used for this purpose.

Particularly, Image Pattern Recognition techniques, as well as predictive algorithms, such as neural networks or the like may be used.

If a predictive algorithm, such as a neural network, is used in combination with the digital images representing the bispectrum, as shown in the previous figures, any pixel of the image may be individually coded. Various coding methods may be provided. One method consists in defining a window of surrounding pixels for each image pixel to be coded, and in using the information regarding the parameters that determine the aspect of the pixel to be coded and those of the pixels of the surrounding pixel window, as parameters of an coding vector for the pixel to be coded. Thus, each pixel is uniquely defined by these parameters and the vector comprising said parameters as coefficients forms the input of the predictive algorithm. As mentioned in the theoretical description of the bispectrum in the graphical representation of the bispectrum the same image is repeated about 12 times, therefore the coding process may be limited to a portion of the bispectrum, such as the portion between lines L1 and L2 in FIG. 17.

Therefore, the number of pixels is dramatically reduced. Furthermore, considering that the window has for instance nine pixels, with the central pixel being the pixel to be coded, the computational load for coding is not excessive.

Hence, the database of bispectrum digital images of sample receive signals comprises, as input variables, the coding vectors for each pixel, as represented by the coefficients of the individual components of said vectors as defined above, and, as output values, the indication as to whether the coded image of each bispectrum of each sample receive signal corresponds to the absence or presence of single microbubbles or small microbubble populations. Such information is coded, for instance, by a vector having two components, e.g. 0 and 1 for the absence of microbubbles, i.e. simple tissue, and 1 and 0 for the presence of microbubbles. These vectors form the output values which are presumptively known from the database of the digital images representing the bispectra of sample receive signals.

The predictive algorithm, e.g. an artificial neural network, is trained by providing it with the input data and the output data of the database. During the training step, the network adjusts the weight of each knot.

Once the network has been trained, it is able to determine whether the digital image representing the bispectrum of the receive signals from a relevant anatomic region relates to simple tissue or to a tissue containing single microbubbles or a small microbubble population.

Obviously, the digital images representing the bispectra of receive signals reflected from the relevant anatomic region should be coded with the same methods that are used for the digital images representing the bispectra of sample receive signals contained in the database of known cases.

Furthermore, the transmit pulses that are used to respectively generate sample receive signals and signals reflected by the relevant anatomic region shall also have similar, preferably identical characteristics.

This method of extraction of the characteristics denoting the presence or absence of single microbubbles or small microbubble populations avoids complex signal analysis, and allows to make a decision as to whether the receive signal contains information denoting the presence of single microbubbles or small microbubble populations, on the basis of the digital images representing the bispectra.

If the receive signal is divided into time blocks, each associated to a segment of the receive signal, then the predictive step shall be performed for the digital image representing the bispectrum of each signal segment of each time block.

While vector coding of the pixels of digital images representing the bispectra is not the only method of coding images for use thereof in combination with a predictive algorithm, said coding method provides an additional advantage in that the coding vector may comprise, for each pixel of the image and pixel window containing the pixel to be coded, certain parameters for describing the aspect of image pixels in the form of time-varying functions. This allows to code each pixel by further adding the segmentation of the receive signal into time blocks. In this case, for each pixel of the digital image representing the bispectrum and for the surrounding pixels of the window as defined above, the coding vector will include the parameters that describe the aspect of said pixels for each time block. Therefore, each component of the coding vector for each pixel to be coded, will be composed of a set of parameters, each being uniquely related to a time block.

Thus, the digital image representing the bispectrum may be coded in such a manner as to also include the segmentation of the receive signal into blocks by one computational step. Also, the predictive algorithm will provide a set of outputs, still by one computational step, which outputs will be the predictions regarding the absence or presence of single microbubbles or small microbubble populations for each of the time blocks composing the receive signal. Digital image coding in combination with predictive algorithms is described in greater detail in EP 1,345,154.

The use of a predictive algorithm as described above shall be only intended as an example of the many available predictive algorithms. The use of so-called CNNs, or Cellular Neural Networks, as described in U.S. Pat. No. 5,140,670 or an Image Pattern Recognition known as ACM and described in greater detail in WO2005/020132.

Figure 14:
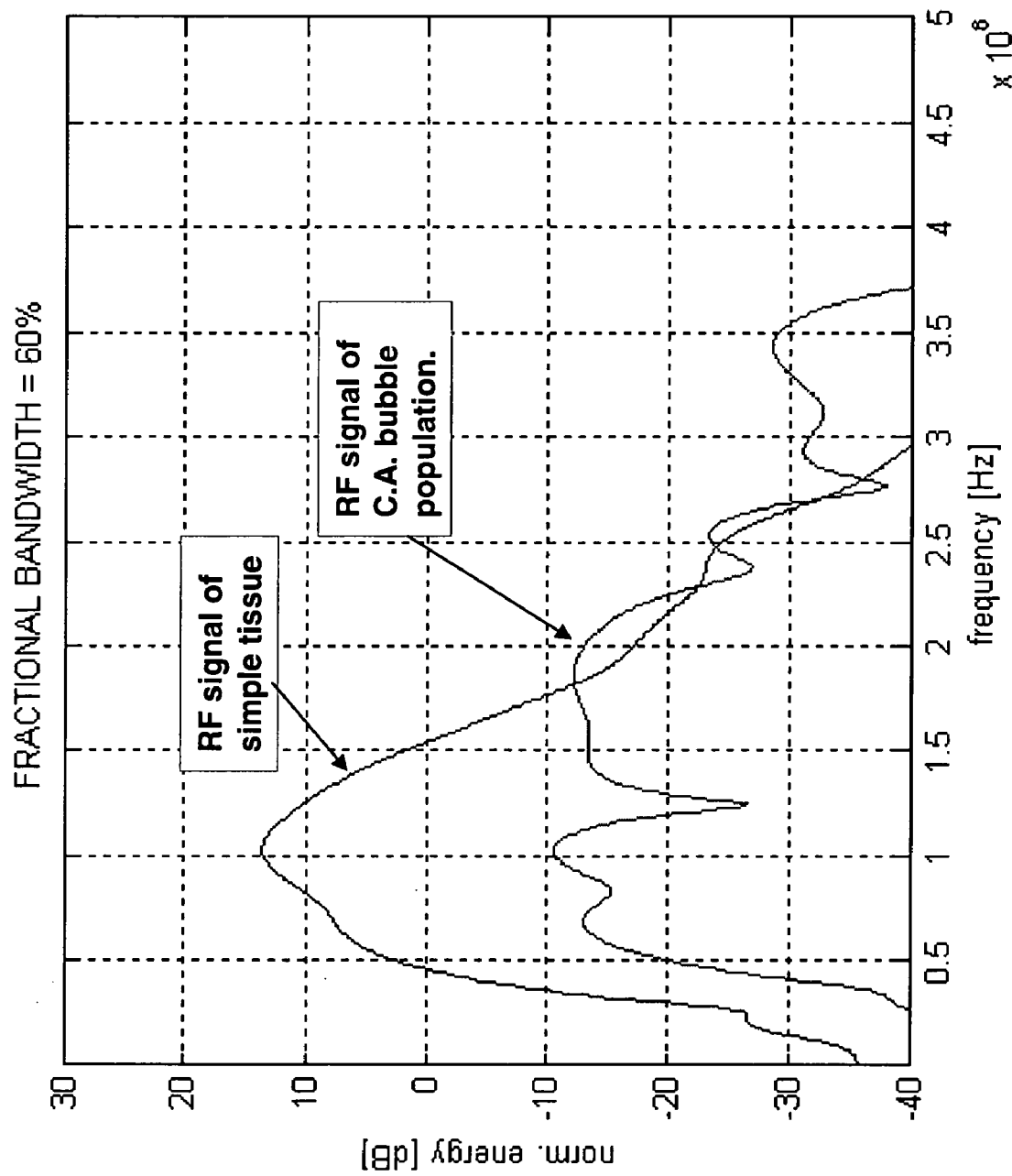
FIG. 14 shows the spectrum of the reflected signal generated by simple tissue and the reflected signal generated by a small microbubble population.

In the foregoing text, the effect of a single microbubble on the receive signal has been always considered in combination with that of a small bubble population. This is perfectly consistent with the above observations. FIG. 14 shows the diagram of the spectral distribution the receive signal energy for a receive signal reflected from simple tissue and a receive signal reflected from a small microbubble population.

Figure 15:
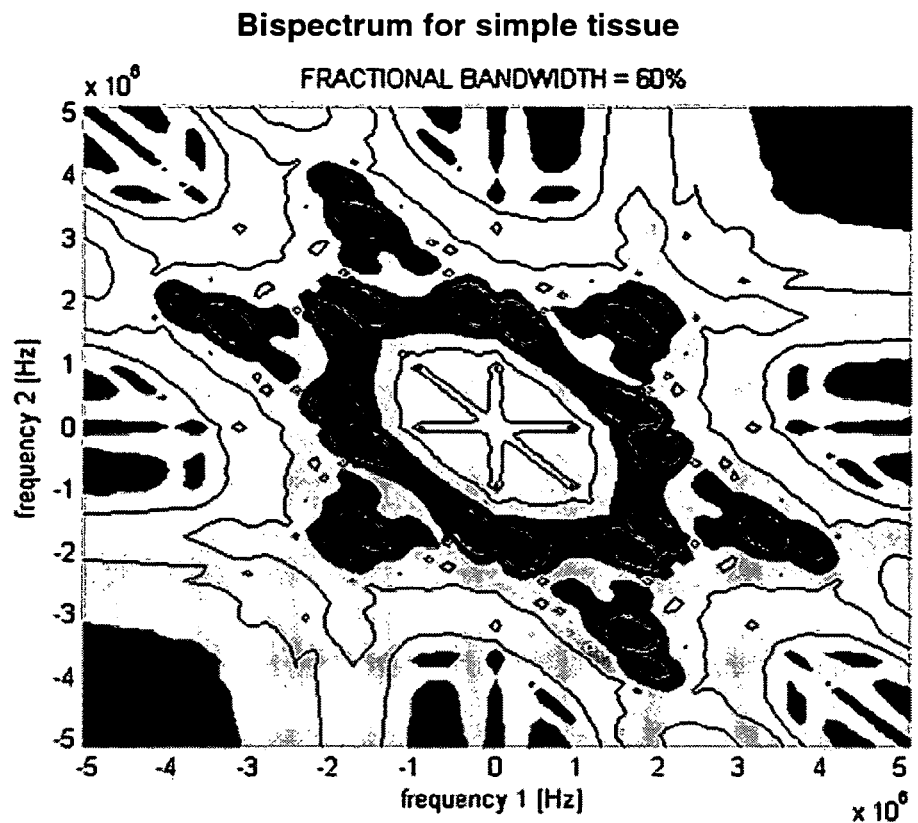
FIGS. 15 and 16 are like FIGS. 12 and 13, except that a small microbubble population is provided in the tissue instead of a single microbubble.
Figure 16:
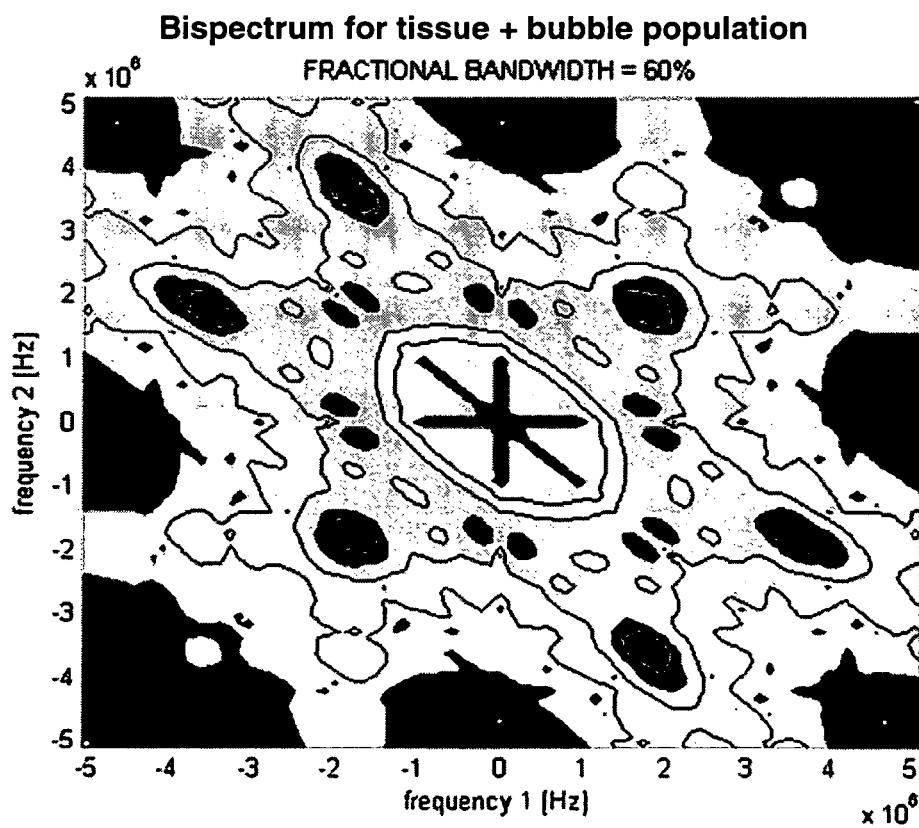

FIG. 15 and 16 show graphic representations of the bispectra of a receive signal resulting from simple tissue and a receive signal resulting from tissue containing a small microbubble population. The comparison of these FIGS. 14, 15 and 16, with FIGS. 5, 12 and 13 clearly shows that the bispectrum can highlight the characteristic differences of the receive signal reflected from a tissue with and without a small microbubble population respectively. The two conditions in which a single microbubble or a small microbubble population are detected respectively may be processed in substantially equivalent manners.

Referring to FIGS. 18 and 19, these show the evolution of the bispectrum image with time (in predetermined steps) along line L1 of FIG. 17. FIGS. 18 and 19 clearly show that, also along said line L1, the bispectrum can highlight the difference between a receive signal reflected from simple tissue, i.e. containing no microbubble, and the receive signal reflected from the tissue containing one microbubble or a small microbubble population.

Once more, such images may be used instead of the digital images representing the bispectrum in combination with predictive algorithms for extracting graphic characteristics therefrom, and for determining whether such characteristics are indicative of the presence of one microbubble or a small microbubble population in the relevant anatomic region.

Figure 20:
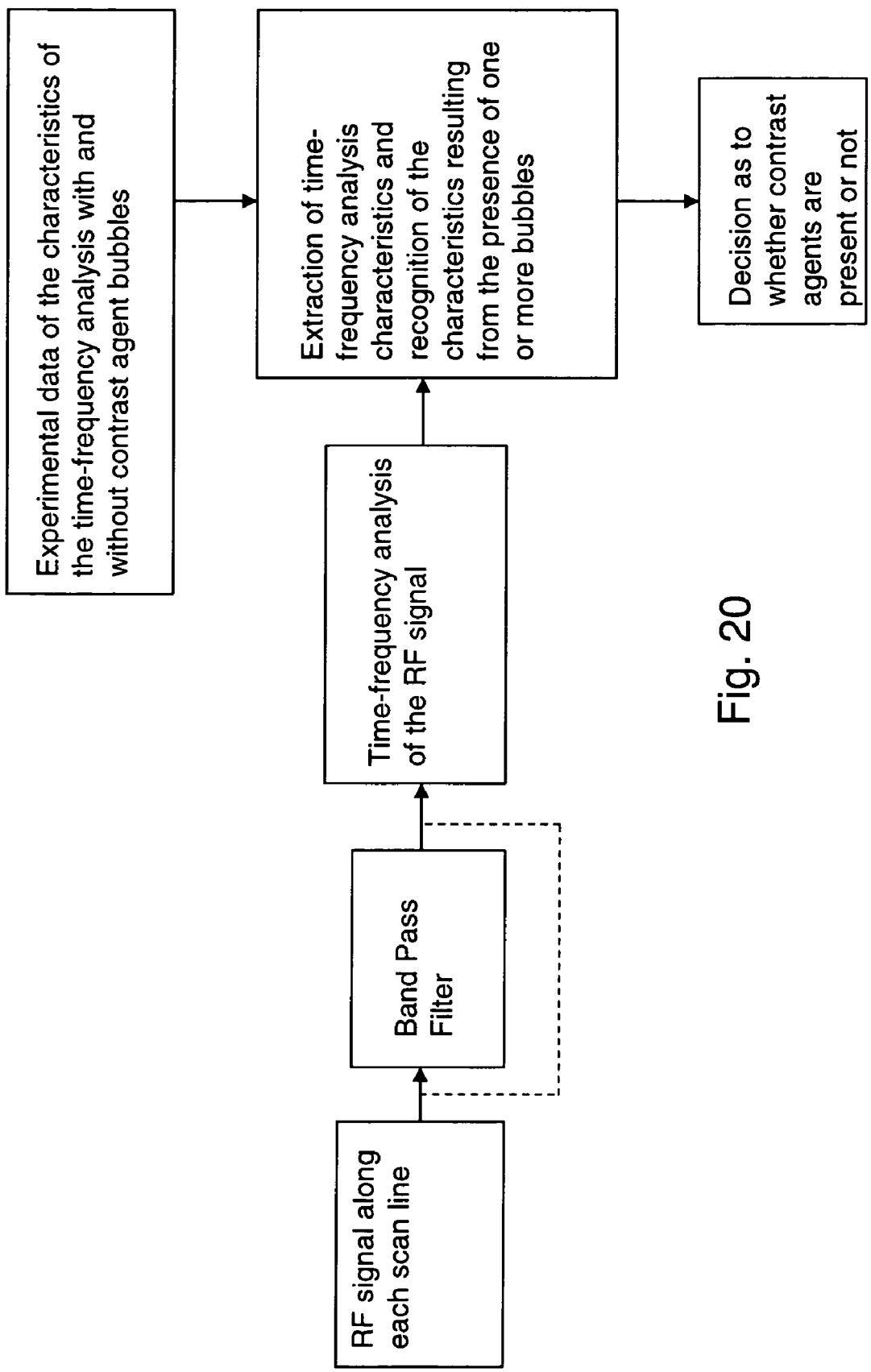
FIG. 20 shows a simplified flow chart of a variant of the inventive method, in which a time-frequency analysis method is used as a multidimensional projection of the reflected signal.

FIG. 20 shows a simplified flow chart, in which a time-frequency analysis method is used as a projection of the receive signal in a multidimensional space.

These methods are also widely known. As shown by the comparison of the flow chart of FIG. 20 with the flow chart of FIG. 3, which describes the previous embodiment, the general steps of the method are essentially identical, whereas the type of projection of the receive signal only changes, therefore for the general steps of the method, reference may be made to the foregoing description of the previous embodiment, as shown in FIGS. 3 to 19, as well as to the description of the principle steps, provided with reference to FIGS. 1 and 2.

In time-frequency analysis of the receive signal, the step of dividing the receive signal into a succession of time blocks, each related to a predetermined time segment of the receive signal is no longer needed as it is obviously integrated in the analysis method itself. Time-frequency analysis of the receive signal is particularly related to the evolution of the analyzed receive signal with time.

A possible time-frequency analysis process is the so-called Gabor expansion or Gabor spectrogram. Such Gabor expansion or Gabor spectrogram is well-known and a more detailed description thereof is contained in: 0817639594; Qian, Shie, Introduction to Time-Frequency and Wavelet Transforms, 1st Ed, Prentice Hall PTR, ISBN: 0130303607.

Figure 21:
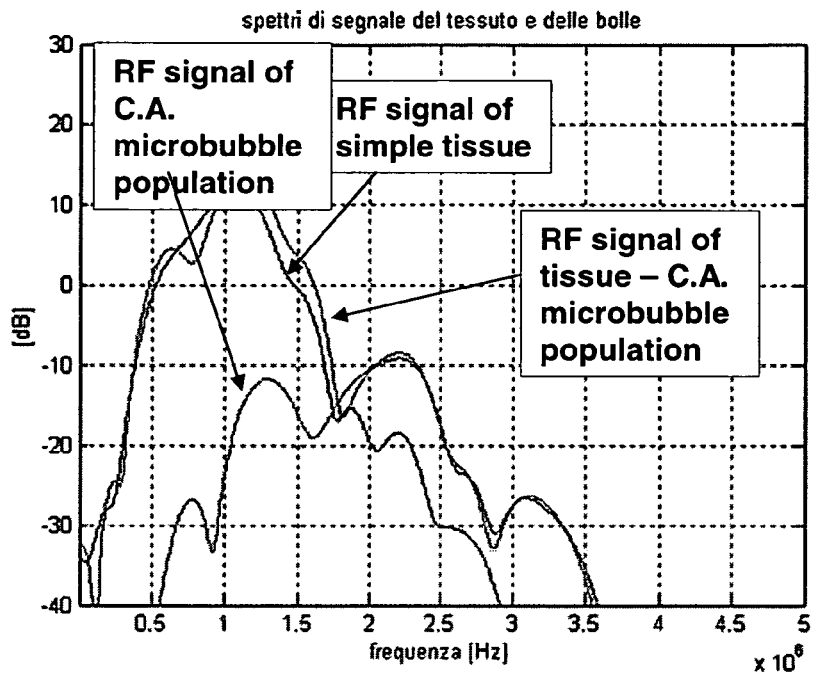
FIGS. 21 and 22 respectively show the spectrum of the receive signals resulting from simple tissue, from microbubbles and from the tissue containing a microbubble population and a time-frequency diagram of the Gabor expansion of the receive signal.

FIG. 21 shows the spectra of the receive signals reflected from simple tissue, from tissue containing one microbubble or a small microbubble, and from the simple microbubble or a small microbubble population.

Figure 22:
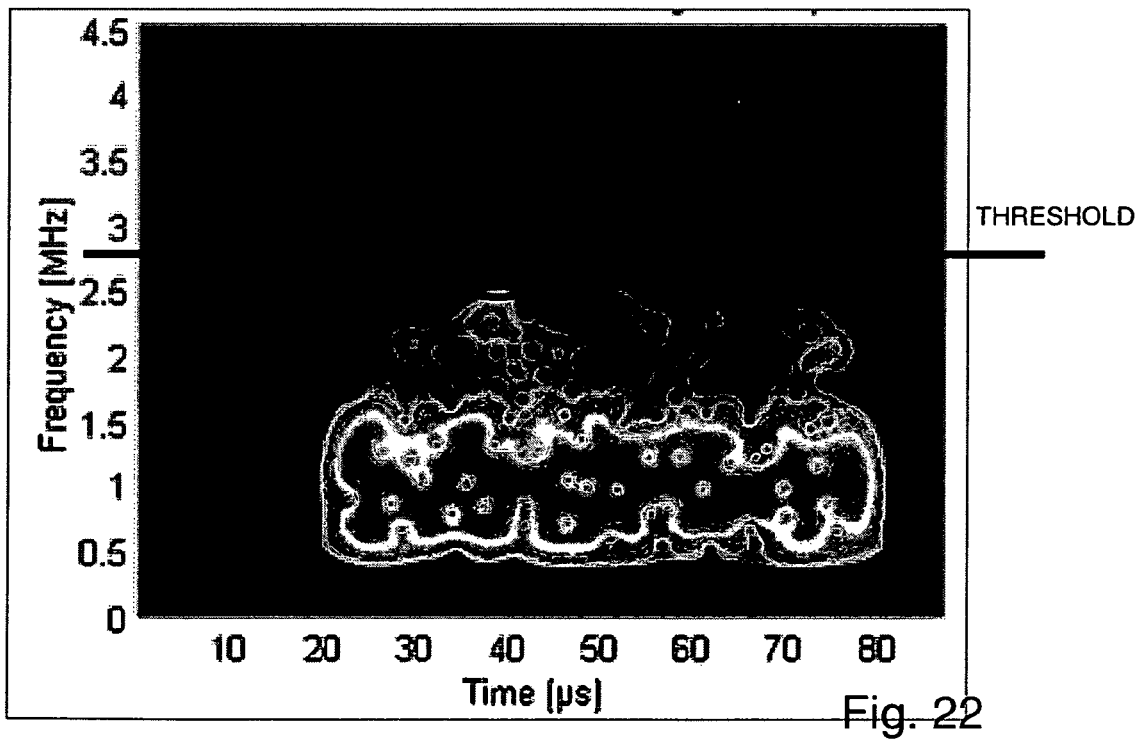

FIG. 22 shows the Gabor expansion of the receive signal for tissue containing one microbubble or a microbubble population. The signal component for the single microbubble or a small microbubble population is indicated by a circle. Here, the presence of such a component may be identified either by applying a threshold to the Gabor expansion modified signal as shown in FIG. 22 or by using Image Pattern Recognition methods as described above with reference to the variant that uses the bispectrum as a projection of the receive signal in the multidimensional space.

For Gabor expansion and more generally for time-frequency analysis methods, the resulting diagram is once again a three-dimensional diagram, the signal energy or strength being shown with respect to a plane defined by a frequency axis and a time axis. Like in the previous embodiment, the images representing the time-frequency analysis in the figures shown frequency against time, whereas the receive signal energy is denoted by a grey scale or false colors.

Therefore, the threshold that is shown in FIG. 22 is not complete, as it only relates to the frequency of one spectral component of the signal. However, the threshold is composed of two components, whereof one is related to the frequency of the spectral component and the other is related to the receive signal energy. This applies to any available method of time-frequency analysis of the receive signal, and also to the next embodiment of a further variant method of time-frequency analysis of the receive signal.

FIG. 22 shows an optimal condition in which Gabor expansion provides good results. In certain conditions, when the energy of the receive signal component associated to the single microbubble is much lower than the same spectral component associated to the non linear behavior of the tissue, Gabor expansion may not be safe in providing information about the presence of microbubbles and localization thereof.

An alternative time-frequency analysis method is the so-called Wigner-Ville distribution. The basic theory of this time-frequency analysis method is described in greater detail in: 0817639594; Qian, Shie, Introduction to Time-Frequency and Wavelet Transforms, 1st Ed, Prentice Hall PTR, ISBN: 0130303607.

Various Wigner Ville Distribution (WVD) variants are available. In the embodiment as described and shown herein, a Pseudo Wigner Ville Distribution (PWVD) variant has been selected.

The basic function that describes such distribution is:

$$W_{xy}(t, \omega) = \int_{-\infty}^{\infty} h(\tau) R_{xy}(t, \tau) e^{-j\omega\tau} d\tau = \int_{-\infty}^{\infty} h(\tau) x(t+\tau/2) y(t-\tau/2) e^{-j\omega\tau} d\tau$$

where:
$h(\tau)$ is a (Gaussian) window function
$x(t)$ is the received signal, filtered between 0.5 and 3.5 MHz
$y(t)$ is the received signal, filtered between 1.7 and 2.3 MHz
The results are more easily readable than those of Wxx, although the information content is essentially the same.

Therefore, a cross-correlation is performed between $x(t)$ and $y(t)$.

It is believed that, while Gabor expansion only highlights the evolution of the signal spectrum with time, PWVD highlights both signal evolution and phase relationships. Therefore, in view of discriminating the receive signals reflected by simple tissue and by tissue containing a single microbubble or a small microbubble population, such Wigner-Ville distribution provides more information than Gabor expansion.

Figures 23, 24:
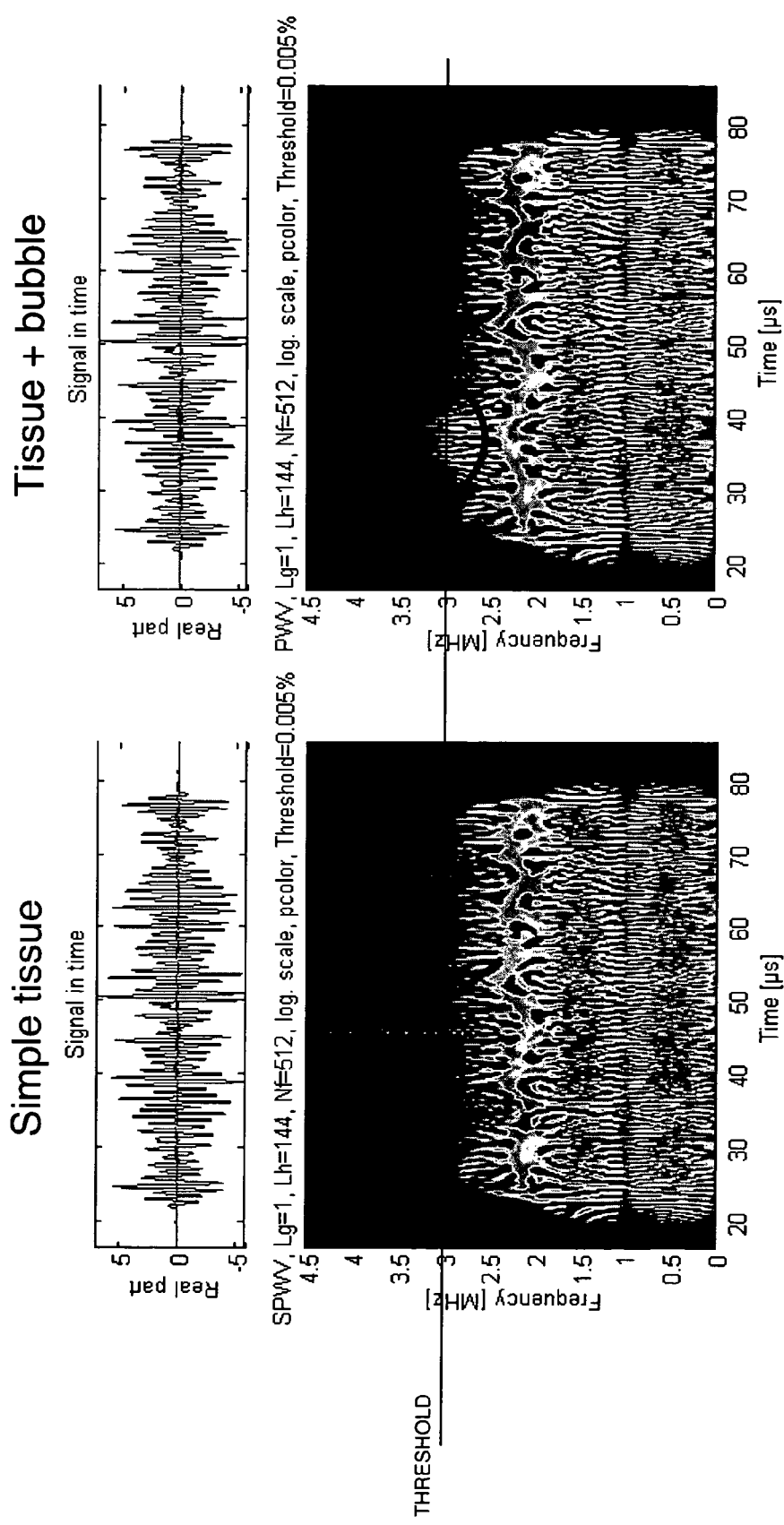
FIG. 23 show the receive signal against time and the graphical representation of the corresponding PWVD (Pseudo Wigner Wille Distribution) of said signal resulting from simple tissue.
FIG. 24 shows charts similar to those of FIG. 23, showing the receive signal generated by the tissue containing a small microbubble population.

FIGS. 23 and 24 and 25 and 26 graphically highlight the effect of PWVD analysis on the signal. In each figure, the receive signal is shown above the PWVD spectrogram. FIGS. 23 and 25 show the receive signal and the corresponding PWVD of a receive signal resulting from simple tissue, whereas FIGS. 24 and 26 show the receive signal and the corresponding PWVD resulting from tissue containing one microbubble or a small microbubble population. The differences between FIGS. 23 and 25 and the corresponding FIGS. 24 and 26 are highlighted in the latter by a circle.

As shown in FIGS. 23 to 26, single bubbles or small microbubble populations may be detected by setting a double frequency and energy threshold for determining the presence of signal contributions above said frequency thresholds and above a minimum signal energy threshold similar to the threshold defined with reference to the previous Gabor expansion embodiment. Like in the Gabor expansion embodiment, once more the threshold may be determined by using known experimental samples to generate a database of sample receive signals to be subjected to PWVD analysis.

As an alternative, Pattern Recognition methods may be also used, like those described with reference to the previous embodiments.

Figure 27:
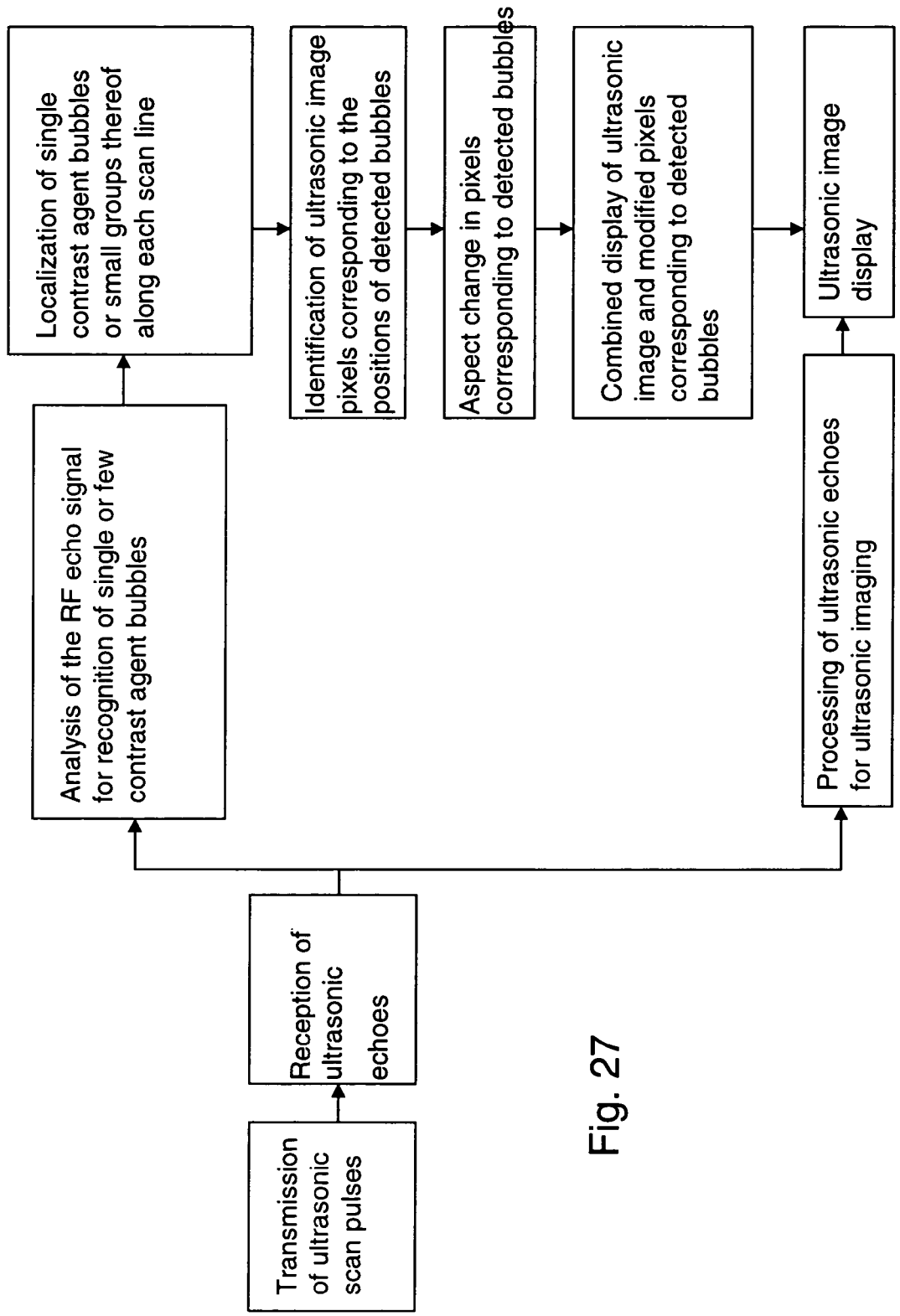

FIG. 27 is a simplified flow chart showing how the results of single microbubble or small microbubble population detection, obtained from the analysis of receive signals, are displayed in parallel with the generation of an ultrasonic image from said signal.

As is apparent from the previous description, the echoes of transmit pulses are received and changed into receive signals. An ultrasonic image, substantially corresponding to a slice of a relevant anatomic region is detected by transmitting ultrasonic pulses along a plurality of adjacent scan lines which are all arranged over the desired scan plane. The receive time for each contribution to the receive signal along the scan line is related to the position of the reflector along the scan line. Thus, each contribution to the receive signal may be related to one or more pixels in a digital image.

This information is also accessible for a parallel processing of the receive signals, including the RF signal analysis steps for recognizing the presence of single contrast agent microbubbles or small microbubble populations according to one of the above methods. Therefore, the single contrast agent microbubbles or small microbubble populations may be localized along each scan line on the basis of the receive time of the receive signal component resulting from the single microbubble or the small microbubble population. Therefore, this information allows to identify the ultrasonic image pixels corresponding to the detected position of the single microbubble or the small microbubble population. The localization of the single microbubble or small microbubble population is simplified when, like in the bispectrum embodiment, the receive signal is divided into a succession of signal time blocks, each comprising a signal segment.

Once the ultrasonic image pixels coinciding with the position of the single microbubble or the small microbubble population have been identified, the aspect of said pixeus is changed, e.g. by adding specific color with respect to the grey-scale ultrasonic image and the pixel/s are displayed in said ultrasonic image with the aspect that has been changed in the previous step. This step in which the single microbubbles or small microbubble populations are localized in an anatomic region under examination and displayed in combination with the ultrasonic image of said anatomic region allows a fast and convenient visual check of the position of the single microbubbles or the small microbubble populations.

Figure 28:
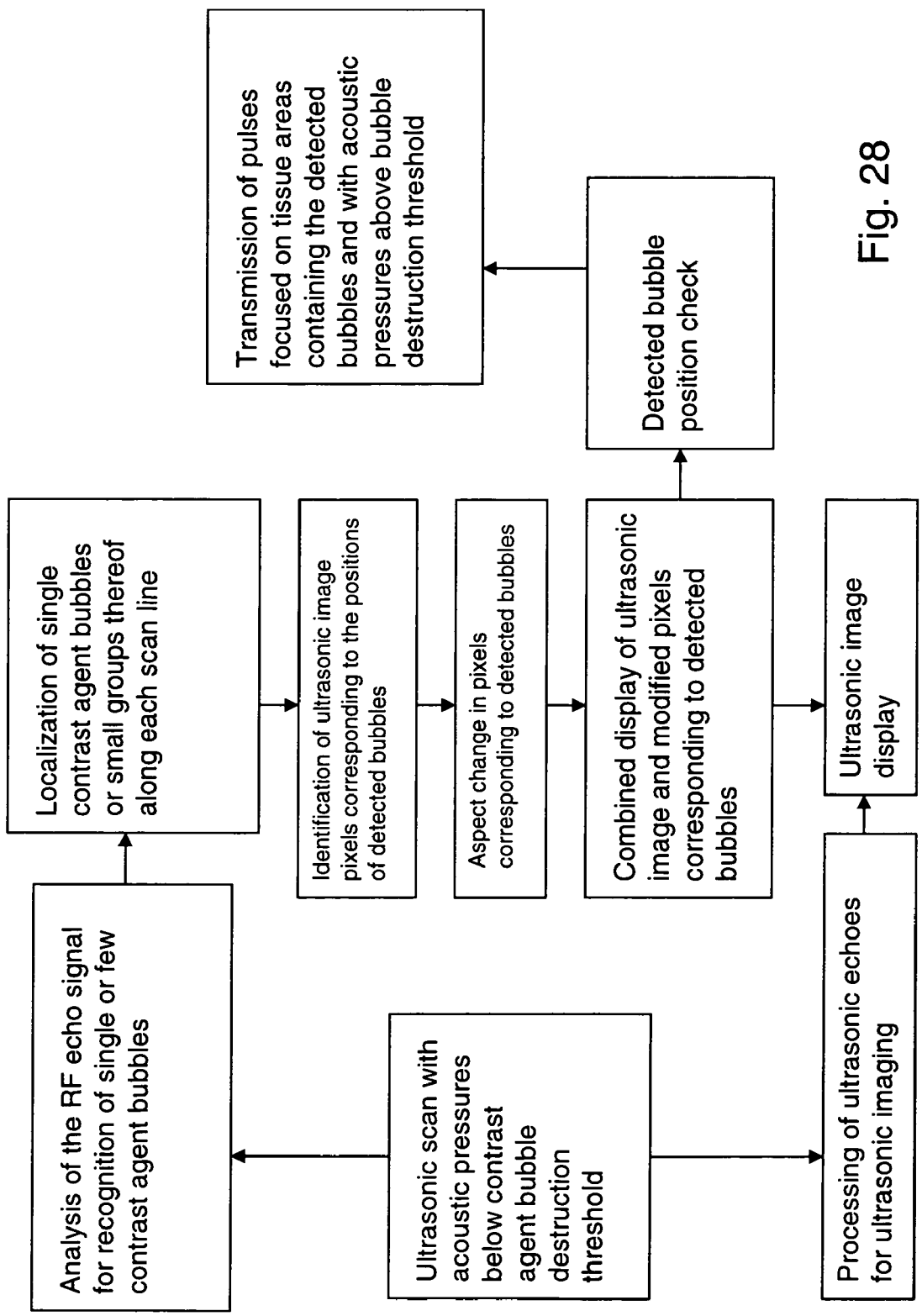
FIG. 28 is a flow chart of a method for local drug administration, which uses microbubbles as drug carriers and a method of detecting the presence and localization of single microbubbles or small microbubble populations according to this invention.

FIG. 28 shows a particular advantageous application of the inventive method for detecting single microbubbles or small microbubble populations, particularly for local drug administration.

The method of the invention is first provided in combination with microbubbles whose structure comprises bioconjugate ligands capable of bonding to specific tissue types, such as particularly, but without limitation, the endothelium of vessels. These microbubbles, which are known as targeted microbubbles, are drawn by the tissues whereto they are capable to bond and bond thereto. A particular application consists in providing microbubbles having bioconjugate ligands capable of bonding to the endothelium particularly of new vessels, to highlight abnormal vascularization conditions indicative of tumor tissues. Other currently studied examples are inflamed tissues or thrombi.

Since the relevant vessels are often as small as microvessels, only a few microbubbles to be detected may pass therethrough or find place therein. Therefore, the combination of the inventive method with the above mentioned targeted microbubbles considerably improves the performances of the diagnostic instrument.

Furthermore, the capability of targeted microbubbles to bond to selected tissue types allows them to be used as carriers, for carrying drugs to the pathologic region and releasing them directly to the pathologic region. This avoids the use of more invasive local drug administration methods, as well as metabolic delivery pathways, e.g. oral administration, which also provides advantages in terms of prevention of the side effects caused by particularly heavy drugs.

Here, the local administration method makes use of an additional characteristic of contrast agent microbubbles. Microbubbles are known to be destroyed by acoustic pressures of ultrasonic transmit pulses incident on said microbubbles. Therefore, once the microbubbles have bonded to the selected tissue and have carried the drug contained therein, they may be detected and the detected position thereof within the relevant anatomic region may be visually checked, so that said microbubbles may be later destroyed by ultrasonic transmit pulses having an acoustic pressure above the resistance limit of said microbubbles, whereby the latter are destroyed and release the drug.

The possibility to detect, display and localize single microbubbles is highly important, even for determining the dose of released drug. In fact, depending on the number of detected microbubbles, the acoustic pressure of the transmit pulse intended for microbubble destruction may be controlled so that only a certain portion of such microbubbles is actually destroyed. Microbubble destruction is well known and is widely used to measure microbubble perfusion in an anatomic region under examination and the skilled person knows that within an acoustic pressure range of a transmit pulse, the acoustic pressure of said pulse only causes a certain portion of microbubbles to be destroyed, according to known ratios of acoustic pressure of the transmit pulse to the number of actually destroyed microbubbles.

Referring to FIG. 28, in which the above described steps of the flow chart of FIG. 27 are repeated on the right side, once the pixels or sets of pixels corresponding to the positions of the single microbubbles or small microbubble populations have been visually highlighted in the ultrasonic image, and a the position of said microbubbles at the proper desired sites has been visually checked, one or more ultrasonic pulses may be transmitted, to be focused on specific areas of the relevant anatomic region, i.e. on the slice corresponding to the displayed image that contains the detected microbubbles, and the acoustic pressures of said transmit pulses may be controlled to levels above the microbubble destruction threshold, to cause the rupture of a certain portion or all of the detected microbubbles.

According to a variant embodiment of the method for detecting single microbubbles or small microbubble populations, the detection data obtained from various projections in different multidimensional spaces may be combined together. For example, simple detection data may be combined by using well known data fusion techniques. As an alternative, the results of each different detection method may be combined.

Hence, for example, the results of multidimensional projections by Higher Order Spectrum or time-frequency analysis techniques, such as one or more Wigner-Ville Distributiori variants and/or such as Gabor expansion or other techniques of multidimensional projection of receive signal spectra may be combined together both before the decision step, in which a decision is made as to whether the signal representation by said projections denotes or not the presence of a single microbubble or a small microbubble population, or after the decision process, on the basis of the receive signal representations according to said projections, the results of said decision step being combined together.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is:

1. A method of ultrasonic detection and localization of contrast agent microbubbles, said method comprising the steps of:
  (a) scanning the relevant anatomic region by transmitting at least one ultrasonic pulse in said region along a plurality of adjacent scan lines;
  (b) receiving the reflected signal along each of said scan lines;
  (c) analyzing the reflected signal along each scan line to identify one signal component deriving from the presence of one microbubble or a small microbubble population and identifying said component of the reflected signal, said analyzing comprising the steps of:
    projecting the reflected signals in one or more multidimensional spaces to highlight the evolution of the reflected signal spectrum with time and/or the phase relationships between reflected signal components having different frequencies or frequency ranges, particularly the signal components at the fundamental frequency of the transmit pulse/s and at the second harmonic of the transmit pulse/s;
    detecting sample reflected ultrasonic signals by transmitting ultrasonic pulses to known tissue samples containing no single microbubble or small microbubble population and on known tissue samples containing a single bubble or a small bubble population;
    projecting the sample reflected ultrasonic signals in the same multidimensional space/s to highlight the evolution of the reflected signal spectrum with time and/ or the phase relationships between the reflected signal components having different frequencies or frequency ranges;

comparing the projections of the sample reflected ultrasonic pulses for simple tissue and tissue having a single microbubble or a small microbubble population in the multidimensional space/s and defining unique characteristics for said projections for simple tissue and tissue having a single microbubble or a small microbubble population;

analyzing the projections of reflected signals in the multidimensional space/s to identify said diversifying characteristics defined on the basis of the comparison between the projections of sample reflected ultrasonic signals in the multidimensional space/s;

defining a projection of the reflected signal in said multidimensional space/s as deriving from a single microbubble or a small microbubble population when it has the characteristics of the projection of the sample reflected ultrasonic signal in said multidimensional space/s relating to the known sample of tissue having a single microbubble or a small microbubble population;

(d) determining the position of the microbubble or the small microbubble population along the corresponding scan line according to the time localization of said component within the duration of the reflected signal, the position of the microbubble or the small microbubble population in the relevant anatomic region being defined by the position of the scan line and the position of the microbubble or the small microbubble population along said scan line; and (e) generating a bispectrum for the signals reflected along each scan line.

2. A method as claimed in claim 1, characterized in that a projection in one or more multidimensional spaces of the receive signal is a Higher Order Spectrum or polyspectrum.

3. A method as claimed in claim 2, characterized by the following steps:

(f) the signals reflected along each scan line or line of view are represented by a bispectrum;

(g) sample reflected ultrasonic signals are detected, by transmitting ultrasonic pulses to known tissue samples containing no single microbubble or small microbubble population and on known tissue samples containing a single bubble or a small bubble population;

(h) the sample reflected ultrasonic signals are also represented by respective bispectra;

(i) the bispectra of the sample reflected ultrasonic pulses for simple tissue and tissue having a single microbubble or a small microbubble population are compared and unique characteristics are defined for said bispectra for simple tissue and tissue having a single microbubble or a small microbubble population;

(j) the bispectra of reflected signals are analyzed to identify said diversifying characteristics defined on the basis of the comparison between the bispectra of sample reflected ultrasonic signals;

(k) the bispectrum of the reflected signal being defined as deriving from a single microbubble or a small microbubble population when it has the characteristics of the bispectrum of the sample reflected ultrasonic signal relating to the known sample of tissue having a single microbubble or a small microbubble population.

4. A method as claimed in claim 2, characterized by the following steps:

(f) the signals reflected along each scan line or line of view are represented by a bispectrum, and a digital image representing said bispectrum is generated;

(g) sample reflected ultrasonic signals are detected, by transmitting ultrasonic pulses to known tissue samples containing no single microbubble or small microbubble population and on known tissue samples containing a single bubble or a small bubble population;

(h) the sample reflected ultrasonic signals are also represented by respective bispectra;

(i) a digital image is generated representing the bispectra of sample reflected ultrasonic signals for simple tissue and for tissue containing a single microbubble or a small microbubble population;

(j) a database of known cases is generated, which comprises the digital images representing the bispectra of sample reflected signals uniquely related to a parameter indicating the association of each bispectra to sample reflected signals resulting from simple tissue or to tissue containing a single microbubble or a small microbubble population;

(k) the database of known cases defined in step i is used to train a predictive algorithm and particularly a neural network;

(l) once the predictive algorithm has been trained according to step k, it is fed with the digital images representing the bispectra of reflected signals, and the output of the predictive algorithm is used as an indicator of the correspondence of the receive signal associated to each digital image representing the bispectra to a reflected signal derived from simple tissue or to a reflected signal deriving from a tissue containing a single microbubble or a small microbubble population.

5. A method as claimed in claim 1, characterized in that a preventive step is provided in which the signal reflected along each scan line is divided into a plurality of successive signal segments, each being associated to a time block of a succession of time blocks having different predetermined start and end times within the overall duration of the receive signal.

6. A method as claimed in claim 1, characterized in that a method of time-frequency analysis of the signal is used as a projection of the signal reflected along the scan lines or lines of view.

7. A method as claimed in claim 6, characterized in that Gabor expansion is used as a time-frequency analysis of the receive signal.

8. A method as claimed in claim 6, characterized in that Wigner-Ville Distribution (WVD) is used as a time-frequency analysis of the receive signal.

9. A method as claimed in claim 6, characterized in that Pseudo Wigner-Ville Distribution (PWVD) is used as a time-frequency analysis of the receive signal.

10. A method as claimed in claim 1, characterized in that the receive signals and sample receive signals are preventively filtered to remove the receive signal component of in the range of the fundamental frequency of transmit pulses.

11. A method as claimed in claim 1, characterized in that it provides parallel processing of receive signals for generating and displaying an ultrasonic image.

12. A method as claimed in claim 1, characterized in that
a time or time window is detected in which, with reference to the overall duration of the receive signal, the portion of the receive signal resulting from one microbubble or a small microbubble population is received and, from such detected time or time window, the position of the microbubble or small microbubble population along the scan line is determined;

a digital ultrasonic image is generated in parallel from the receive signal of each scan line;

the time or time window in which the portion of the receive signal resulting from reflection from one microbubble or a small microbubble population is received along a predetermined scan line, is used to determine the pixel or set of pixels of the digital ultrasonic image which correspond to said receive time or said receive time window and to the scan line;

the aspect of said pixel or said set of pixels is changed to be different from the aspect of the ultrasonic image pixels;

said pixel or said set of pixels is displayed with its changed aspect in the digital ultrasonic image.

13. A method as claimed in claim 1, characterized in that the presence of one microbubble or a small microbubble population is detected by projecting the receive signals in multidimensional spaces according to two, three or more different multidimensional projections, the data of all of said multidimensional projections being combined by data fusion techniques and the presence of one microbubble or a small microbubble population being determined on the basis of the data of each of said multidimensional projections of the receive signals.

14. A method as claimed in claim 1, characterized in that the presence of one microbubble or a small microbubble population is detected by projecting the receive signals in multidimensional spaces according to two, three or more different multidimensional projections, the presence of one microbubble or a small microbubble population being determined by a combination of the results of the detection of one microbubble or a small microbubble population that were obtained from each of said multidimensional projections.

* * * * *